(12) United States Patent
MacKinnon et al.

(10) Patent No.: US 7,692,784 B2
(45) Date of Patent: Apr. 6, 2010

(54) APPARATUS AND METHODS RELATING TO ENHANCED SPECTRAL MEASUREMENT SYSTEMS

(75) Inventors: Nicholas B. MacKinnon, Vancouver (CA); Ulrich Stange, Vancouver (CA)

(73) Assignee: Tidal Photonics, Inc., Vancouver, British Columbia (CA)

( * ) Notice: Subject to any disclaimer, the term of this patent is extended or adjusted under 35 U.S.C. 154(b) by 1008 days.

(21) Appl. No.: 10/952,374

(22) Filed: Sep. 27, 2004

(65) Prior Publication Data

US 2005/0213092 A1 Sep. 29, 2005

Related U.S. Application Data

(60) Provisional application No. 60/506,408, filed on Sep. 26, 2003.

(51) Int. Cl.
G01J 3/00 (2006.01)
G01J 3/42 (2006.01)
G01J 3/427 (2006.01)
G01J 3/28 (2006.01)

(52) U.S. Cl. .................. 356/300; 356/319; 356/326; 356/328

(58) Field of Classification Search .............. None
See application file for complete search history.

(56) References Cited

U.S. PATENT DOCUMENTS

| 4,158,505 A | 6/1979 | Mathisen et al. |
|---|---|---|
| 4,175,545 A | 11/1979 | Termanini |
| 4,204,528 A | 5/1980 | Termanini |
| 4,401,124 A | 8/1983 | Guess et al. |
| 4,407,294 A | 10/1983 | Vilkomerson |
| 4,582,061 A | 4/1986 | Fry |
| 4,706,681 A | 11/1987 | Breyer et al. |
| 4,739,396 A | 4/1988 | Hyatt |
| 4,763,993 A | 8/1988 | Vogeley et al. |
| 4,782,386 A | 11/1988 | Ams et al. |
| 4,843,529 A | 6/1989 | Izenour |
| 4,848,880 A | 7/1989 | Aull et al. |
| 4,858,001 A | 8/1989 | Milbank et al. |
| 4,867,563 A | 9/1989 | Wurm et al. |
| 4,885,634 A | 12/1989 | Yabe |
| 4,890,208 A | 12/1989 | Izenour |

(Continued)

FOREIGN PATENT DOCUMENTS

AU 2007200111 A1 2/2007

(Continued)

OTHER PUBLICATIONS

International Search Report, PCT/CA2004/001762, Feb. 16, 2005.

(Continued)

Primary Examiner—Tarifur Chowdhury
Assistant Examiner—Gordon J Stock, Jr.
(74) Attorney, Agent, or Firm—Joshua King; Graybeal Jackson LLP

(57) ABSTRACT

The apparatus and methods herein provide light sources and spectral measurement systems that can improve the quality of images and the ability of users to distinguish desired features when making spectroscopy measurements by providing methods and apparatus that can improve the dynamic range of data from spectral measurement systems.

18 Claims, 9 Drawing Sheets

U.S. PATENT DOCUMENTS

| | | | |
|---|---|---|---|
| 4,937,448 A * | 6/1990 | Mantz et al. | 250/343 |
| 4,955,385 A | 9/1990 | Kvalo et al. | |
| 5,037,173 A | 8/1991 | Sampsell et al. | |
| 5,090,807 A | 2/1992 | Tai | |
| 5,092,331 A | 3/1992 | Nakamura | |
| 5,121,239 A | 6/1992 | Post | |
| 5,233,459 A | 8/1993 | Bozler et al. | |
| 5,256,869 A | 10/1993 | Lin et al. | |
| 5,259,837 A | 11/1993 | Van Wormer | |
| 5,270,797 A | 12/1993 | Pollak et al. | |
| 5,351,151 A | 9/1994 | Levy | |
| 5,369,481 A | 11/1994 | Berg et al. | |
| 5,409,000 A | 4/1995 | Imran | |
| 5,409,009 A | 4/1995 | Olson | |
| 5,432,543 A | 7/1995 | Hasegawa et al. | |
| 5,440,388 A | 8/1995 | Erickson | |
| 5,461,475 A | 10/1995 | Lerner et al. | |
| 5,474,519 A | 12/1995 | Bloomer | |
| 5,528,368 A | 6/1996 | Lewis et al. | |
| 5,555,085 A | 9/1996 | Bogdanowicz et al. | |
| 5,587,832 A | 12/1996 | Krause | |
| 5,604,566 A | 2/1997 | Mano et al. | |
| 5,748,308 A * | 5/1998 | Lindberg et al. | 356/310 |
| 5,754,278 A | 5/1998 | Kurtz | |
| 5,796,508 A | 8/1998 | Suzuki | |
| 5,805,213 A | 9/1998 | Spaulding et al. | |
| 5,828,485 A | 10/1998 | Hewlett | |
| 5,926,773 A * | 7/1999 | Wagner | 702/22 |
| 5,938,319 A | 8/1999 | Hege | |
| 6,046,808 A * | 4/2000 | Fateley | 356/330 |
| 6,075,563 A * | 6/2000 | Hung | 348/223.1 |
| 6,110,106 A | 8/2000 | MacKinnon et al. | |
| 6,128,077 A | 10/2000 | Jovin et al. | |
| 6,128,078 A | 10/2000 | Fateley | |
| 6,191,802 B1 | 2/2001 | Kessler | |
| 6,204,941 B1 | 3/2001 | Beale et al. | |
| 6,265,708 B1 | 7/2001 | Tanaka et al. | |
| 6,303,916 B1 | 10/2001 | Gladnick | |
| 6,337,760 B1 | 1/2002 | Huibers et al. | |
| 6,356,378 B1 | 3/2002 | Huibers | |
| 6,369,933 B1 | 4/2002 | O'Callaghan | |
| 6,412,972 B1 | 7/2002 | Pujol et al. | |
| 6,436,127 B1 | 8/2002 | Anderson et al. | |
| 6,437,919 B1 | 8/2002 | Brown et al. | |
| 6,459,919 B1 | 10/2002 | Lys et al. | |
| 6,464,633 B1 * | 10/2002 | Hosoda et al. | 600/178 |
| 6,485,414 B1 | 11/2002 | Neuberger | |
| 6,490,017 B1 | 12/2002 | Huang et al. | |
| 6,504,943 B1 | 1/2003 | Sweatt et al. | |
| 6,545,758 B1 | 4/2003 | Sandstrom | |
| 6,567,163 B1 | 5/2003 | Sandstrom | |
| 6,567,217 B1 | 5/2003 | Kowarz et al. | |
| 6,567,543 B1 | 5/2003 | Shiraiwa et al. | |
| 6,618,184 B2 | 9/2003 | Jin et al. | |
| 6,646,633 B1 | 11/2003 | Nicolas | |
| 6,657,758 B1 | 12/2003 | Garner | |
| 6,663,560 B2 | 12/2003 | MacAulay et al. | |
| 6,710,909 B2 | 3/2004 | Naito | |
| 6,781,691 B2 | 8/2004 | MacKinnon et al. | |
| 6,806,954 B2 | 10/2004 | Sandstrom | |
| 6,824,283 B2 | 11/2004 | Pohlert et al. | |
| 6,842,549 B2 * | 1/2005 | So | 385/15 |
| 6,859,275 B2 | 2/2005 | Fateley et al. | |
| 6,878,109 B2 | 4/2005 | Yamaki et al. | |
| 6,882,770 B2 | 4/2005 | Neilson et al. | |
| 6,900,825 B2 | 5/2005 | Kito | |
| 6,909,459 B2 | 6/2005 | Watson, Jr. et al. | |
| 6,996,292 B1 | 2/2006 | Gentry et al. | |
| 7,019,908 B2 | 3/2006 | Van 't Spijker et al. | |
| 7,108,402 B2 | 9/2006 | MacKinnon et al. | |
| 7,151,601 B2 | 12/2006 | MacKinnon et al. | |
| 7,196,789 B2 * | 3/2007 | Senturia et al. | 356/323 |
| 7,274,500 B2 | 9/2007 | Kowarz | |
| 7,342,658 B2 * | 3/2008 | Kowarz et al. | 356/328 |
| 7,511,871 B2 | 3/2009 | MacKinnon et al. | |
| 7,544,163 B2 | 6/2009 | MacKinnon et al. | |
| 2001/0052977 A1 | 12/2001 | Toyooka | |
| 2002/0057431 A1 | 5/2002 | Fateley et al. | |
| 2002/0113881 A1 | 8/2002 | Funston et al. | |
| 2002/0156349 A1 | 10/2002 | Yamaki et al. | |
| 2002/0161283 A1 | 10/2002 | Sendai | |
| 2002/0176151 A1 | 11/2002 | Moon et al. | |
| 2002/0180973 A1 | 12/2002 | MacKinnon et al. | |
| 2003/0107732 A1 | 6/2003 | Sasaki et al. | |
| 2003/0174324 A1 | 9/2003 | Sandstrom | |
| 2003/0187330 A1 | 10/2003 | Abe | |
| 2004/0218172 A1 * | 11/2004 | DeVerse et al. | 356/300 |
| 2004/0233448 A1 * | 11/2004 | Goulas et al. | 356/432 |
| 2005/0063079 A1 | 3/2005 | MacKinnon et al. | |
| 2005/0234302 A1 | 10/2005 | MacKinnon et al. | |
| 2005/0251230 A1 | 11/2005 | MacKinnon et al. | |
| 2008/0212980 A1 * | 9/2008 | Weiner | 398/184 |
| 2008/0260242 A1 | 10/2008 | MacKinnon et al. | |
| 2009/0012361 A1 | 1/2009 | MacKinnon et al. | |

FOREIGN PATENT DOCUMENTS

| | | |
|---|---|---|
| AU | 2002231504 B2 | 8/2007 |
| AU | 2007205778 A1 | 8/2007 |
| CA | 2404600 A1 | 10/2001 |
| CA | 2388696 A1 | 2/2002 |
| CA | 2474832 A1 | 8/2002 |
| CA | 2380765 A1 | 10/2002 |
| CA | 2461599 | 4/2003 |
| CA | 2581656 A1 | 4/2005 |
| CA | 2581660 A1 | 4/2005 |
| CA | 2581668 A1 | 4/2005 |
| CA | 2581697 A1 | 4/2005 |
| CA | 2581735 A1 | 4/2005 |
| EP | 0008639 A1 | 3/1980 |
| EP | 1304019 A1 | 4/2003 |
| EP | 1360438 A2 | 11/2003 |
| EP | 1656584 A2 | 5/2006 |
| EP | 1709405 A1 | 10/2006 |
| EP | 1709474 A1 | 10/2006 |
| EP | 1709475 A1 | 10/2006 |
| EP | 1709476 A1 | 10/2006 |
| EP | 1713540 A2 | 10/2006 |
| GB | 2377280 A | 1/2003 |
| JP | 04297225 | 10/1992 |
| JP | 06207853 | 7/1994 |
| JP | 08185986 | 7/1996 |
| JP | 11101944 | 4/1999 |
| JP | 11295219 | 10/1999 |
| JP | 2000504115 | 4/2000 |
| JP | 2000195683 | 7/2000 |
| JP | 2003010101 | 1/2003 |
| JP | 2004526188 | 8/2004 |
| JP | 2007-506994 | 3/2007 |
| JP | 2007506485 | 3/2007 |
| JP | 2007506486 | 3/2007 |
| JP | 2007506487 | 3/2007 |
| JP | 2007506947 | 3/2007 |
| JP | 2007-534973 | 11/2007 |
| WO | WO 9852386 | 11/1998 |
| WO | WO 0182778 A2 | 11/2001 |
| WO | WO 0201921 | 1/2002 |
| WO | WO 02063206 A2 | 8/2002 |
| WO | WO 03029791 A1 * | 4/2003 |
| WO | WO 2005010597 | 2/2005 |
| WO | WO 2005030328 A2 | 4/2005 |
| WO | WO 2005031292 A1 | 4/2005 |
| WO | WO 2005031433 A1 | 4/2005 |
| WO | WO 2005031434 A1 | 4/2005 |

WO WO 2005031436 A1 4/2005

OTHER PUBLICATIONS

Davidson et al., (1999) Optical Society of America, 24(24):1835.
International Search Report, International Application No. GB0207826.9, dated Oct. 30, 2002.
International Search Report, International Application No. PCTCA2002000124, Dated Aug. 19, 2002.
International Search Report, International Application No. PCTCA2004001748, Dated Feb. 16, 2005.
International Search Report, International Application No. PCTCA2004001749, Dated Feb. 23, 2005.
International Search Report, International Application No. PCTCA2004001751, Dated Feb. 16, 2005.
International Search Report, International Application No. PCTCA2004001752, Dated Feb. 16, 2005.
International Search Report, International Application No. PCTUS2004022977, Dated Oct. 4, 2006.
Office Action, U.S. Appl. No. 10/061,966, Dated Nov. 20, 2003.
U.S. Appl. No. 60/506,273, filed Sep. 26, 2003, Titled, "Apparatus and Methods Relating to Expanded Dynamic Range Imaging Endoscope Systems," Now Expired.
U.S. Appl. No. 11/473,506, filed Jun. 22, 2006, Titled, "Apparatus and Methods for Measuring and Controlling Illumination for Imaging Objects, Performances and the Like," Now Abandoned.
U.S. Appl. No. 11/496,960, filed Jul. 31, 2006, Titled, "Apparatus and Methods Relating to Wavelength Conditions of Illumination," Now Abandoned.
U.S. Appl. No. 11/709,340, filed Feb. 20, 2007, Titled, "Apparatus and Methods for Measuring and Controlling Illumination for Imaging Objects, Performances and the Like," Now Abandoned.
U.S. Appl. No. 11/725,987, filed Mar. 19, 2007, Titled, "Apparatus and Methods Relating to Wavelength Conditioning of Illumination," Now Abandoned.
U.S. Appl. No. 11/983,752, filed Nov. 9, 2007, Titled, "Apparatus and Methods Relating to Wavelength Conditioning of Illumination," Now Abandoned.
U.S. Appl. No. 12/176,269, filed Jul. 18, 2008, Titled, "Apparatus and Methods Relating to Wavelength Conditioning of Illumination," Now Abandoned.
U.S. Appl. No. 12/197,988, filed Aug. 25, 2008, Titled, "Apparatus and Methods for Performing Phototherapy, Photodynamic Therapy and Diagnosis," Now Abandoned.
U.S. Appl. No. 12/433,733, filed Apr. 30, 2009, Titled, "Apparatus and Methods Relating to Expanded Dynamic Range Imaging Endoscope Systems".
U.S. Appl. No. 12/242,671, filed Sep. 30, 2008, Titled, "Apparatus and Methods Relating to Wavelength Conditioning of Illumination".
Supplemental European Search Report Dated Nov. 26, 2009, for European Patent Publication No. EP 1709474 Published Oct. 11, 2006.

* cited by examiner

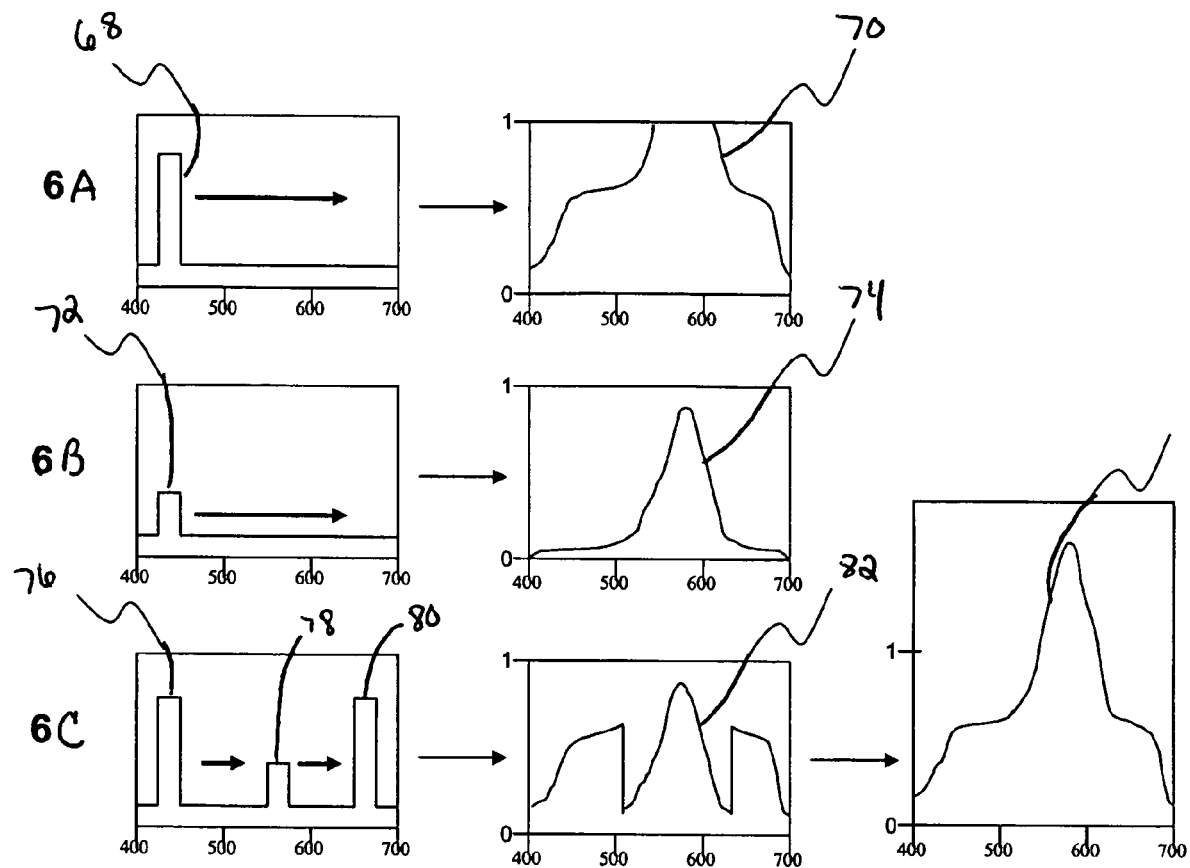
Figs 6A-C

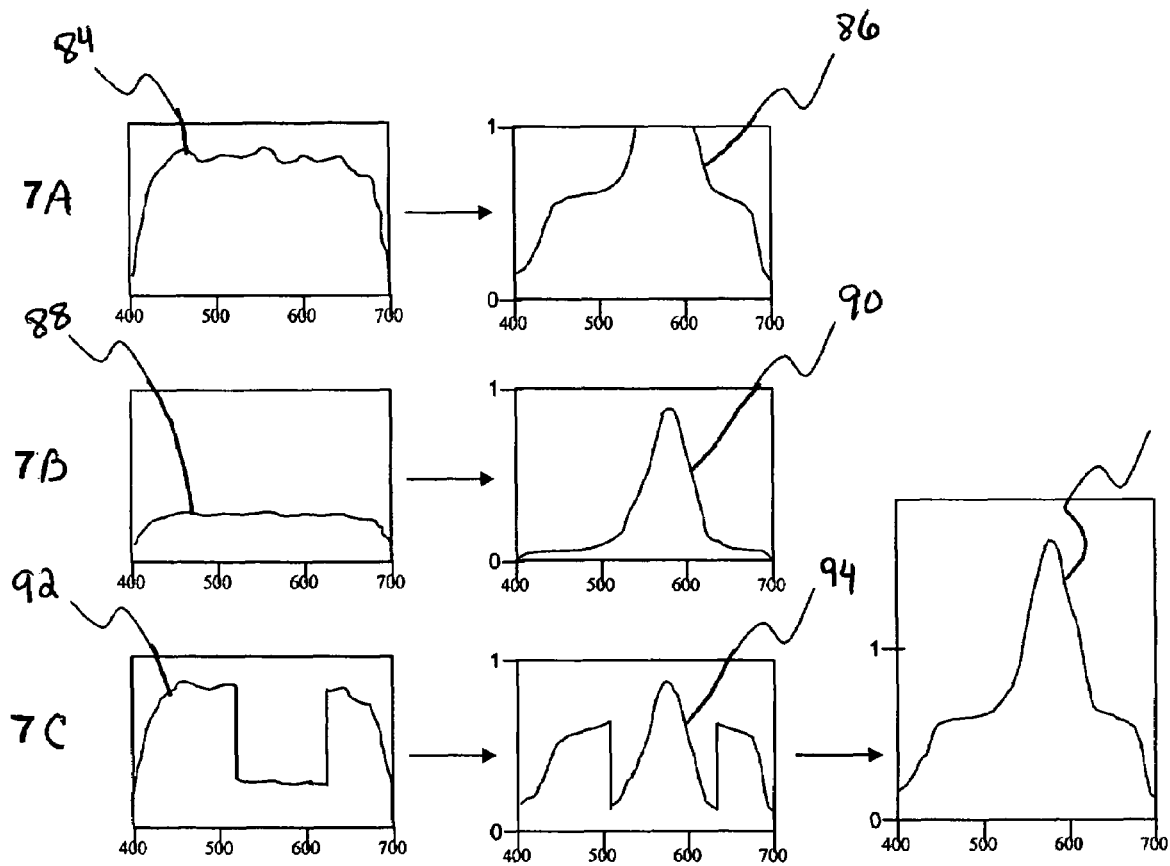
Figs 7A-C

APPARATUS AND METHODS RELATING TO ENHANCED SPECTRAL MEASUREMENT SYSTEMS

CROSS-REFERENCE TO RELATED APPLICATIONS

The present application claims priority from pending U.S. provisional patent application No. 60/506,408 filed 26 Sep. 2003.

BACKGROUND

Optical spectroscopy is a known method of measuring the optical properties of a material such as gas, liquid, solid, chemical compound, biological material such as biological fluids or tissue, paint or coating or other material.

A common form of spectroscopy measures the spectral properties of the desired material by illuminating the material with light and then measuring the light remitted or emitted by a material. The relative response of the material to light of different energy levels is useful characteristic of a material, sometimes called the optical signature that can be used to identify the nature of a material or determine how much of a material is present.

When there is a mixture of materials the optical signature of the mixture is typically some combination of the optical signatures of the components of the mixture. Analysis of the relative amounts of wavelengths characteristic of a particular material either by visual inspection, or more commonly by computer based algorithms, can be used to determine how much of a material is present in the mixture.

The optical signatures or spectra of a material are typically represented as an intensity of emission or absorbance at a particular wavelength or wavelength range and are often presented as a two dimensional graph with wavelength on one axis and intensity or absorbance as a function of wavelength on the other axis. These graphs can be simple or complex in shape and the range between intensities or absorbance can be very great for different wavelengths.

The measurement tools used to measure the intensity of absorbance or emission of light from a compound are usually referred to as spectrographs or spectrometers and are well known. One limitation of these devices is the difficulty of making accurate measurements over wide ranges of intensity values.

Considering the case of reflectance spectroscopy, for some samples the light emitted from a sample may be very bright at some wavelengths of interest and very faint at others. Often the detector measurement range is exceeded.

Detectors also often have their own wavelength response due to the spectral properties of the detection system, which can further limit the capability to make an accurate measurement.

Most spectrometers are designed to work with a light source suitable for illuminating the material to be measured to provide wavelengths useful for measurement of the desired optical properties of the material. The measurement device is typically calibrated against the optical properties of the light source. This can also become a limiting factor in the ability of the system to make measurements since some light sources do not provide enough of the wavelengths useful for the measurement.

Often a spectrograph or spectrometer system has to be set up for a particular application or a material to be measured and is difficult to reconfigure quickly for the measurement of a wide range of compounds.

Thus there has gone unmet a need for spectral measurement systems and spectroscopy light sources that provide improved dynamic range and improved accuracy, and can be configured quickly to measure accurately a wide range of samples.

SUMMARY

The apparatus and methods, etc., herein provide spectral measurement systems (i.e., systems that measure the wavelength dependent intensity distribution of light emanating from a sample) such as spectroscopy systems, the spectral measurement systems comprising a computer-controlled illumination system (CCIS) and an operably linked spectral measurement sensor (SMS), which can be an operably linked computer-controlled spectral measurement sensor (CCSMS). The CCIS works interactively with the SMS to produce enhanced measurements such as measurements with expanded dynamic range, improved measurement signal to noise ratio, or improved accuracy.

The computer-controlled illumination system comprises a tunable light source capable of providing illumination light having a variable selected spectral output and a variable wavelength dependent intensity distribution. In certain embodiments, the CCIS comprises a bright source of broadband visible illumination commonly called white light, a spectrum former such as a prism or diffraction grating, and a spatial light modulator (SLM) such as a pixelated SLM, or other suitable tunable devices such as transmissive SLMs, reflective SLMs, tunable devices such as transmissive SLMs, reflective SLMs (such as digital micromirror devices (DMDs) or liquid crystal on silicon devices (LCOSs)), or acousto-optic tunable filters (AOTFs). For example, the light from the light source is directed as a beam to the wavelength dispersive element, which disperses the beam into a spectrum imaged onto the SLM. The pixel elements (or other light control elements) of the SLM can be rapidly switched to allow selected wavelengths of light and selected amounts of the selected wavelengths of light to form the illumination light and to propagate. The light that propagates is then optically mixed together and directed to the illumination path of a spectroscopy device or system.

While the use of white light is one preferred embodiment of the CCIS, it is also possible to use other wavelengths for example ultraviolet or infrared, or to use narrower bands of illumination or light sources with strong characteristic emissions which may be useful for measurements, for example a mercury arc lamp which has strong emissions at 365 nm, 405 nm, 436 nm, 546 nm and other wavelengths, which may be useful for exciting fluorescence.

The SLM is operably connected to a controller, which controller contains computer-implemented programming that controls the on/off pattern of the pixels in the SLM. The controller can be located in any desired location to the rest of the system. For example, the controller can be either within a housing of the source of illumination or it can be located remotely, connected by a wire, fiber optic cable, cellular link or radio link to the rest of the system. If desired, the controller, which is typically a single computer but can be a plurality of linked computers, a plurality of unlinked computers, computer chips separate from a full computer or other suitable controller devices, can also contain one or more computer-implemented programs that provide specific lighting characteristics, i.e., specific desired, selected spectral outputs and wavelength dependent intensities, corresponding to known wavelength bands that are suitable for measuring the spectral property of a sample material.

In one aspect, the present apparatus and methods provides a CCIS that provides a variable selected spectral output and a variable selected wavelength dependent intensity distribution wherein the CCIS comprises a light path that comprises: a) a spectrum former able to provide a spectrum from a light beam traveling along the light path, and b) a pixelated SLM located downstream from and optically connected to the spectrum former, the pixelated SLM reflecting substantially all light impinging on the SLM and in some embodiments switchable to reflect light from the light beam between at least first and second reflected light paths in which at least one or more of the light paths do not reflect back to the spectrum former. The SLM can, for example, be a digital micromirror device or LCOS. The SLM is operably connected to at least one controller containing computer-implemented programming that controls an on/off pattern of pixels in the pixelated SLM to reflect a desired segment of light in the spectrum to the first reflected light path and reflect substantially all other light in the spectrum impinging on the SLM to another light path, the desired segment of light consisting essentially of a desired selected spectral output and a desired wavelength dependent intensity distribution.

The spectrum former can comprise at least one of a prism and a diffraction grating, which can be a reflective diffraction grating, transmission diffraction grating, variable wavelength optical filter, or a mosaic optical filter. The system may or may not comprise, between the spectrum former and the SLM, an enhancing optical element that provides a substantially enhanced image of the spectrum from the spectrum former to the SLM. The SLM can be a first SLM, and the desired segment of light can be directed to a second SLM operably connected to the same controller or another controller containing computer-implemented programming that controls an on/off pattern of pixels in the second SLM to reflect the desired segment or other segment of light in one direction and reflect other light in the spectrum in at least one other direction. The system can further comprise an optical projection device located downstream from the first SLM to project light out of the lighting system as a directed light beam.

The CCIS can further comprise an illumination light detector optically connected to and downstream from the SLM, the illumination light detector also operably connected to a controller containing computer-implemented programming able to determine from the illumination light detector whether the desired segment contains a desired selected spectral output and a desired wavelength dependent intensity distribution, and adjust the on/off pattern of pixels in the pixelated SLM to improve the correspondence between the desired segment and the desired selected spectral output and the desired wavelength dependent intensity distribution. The illumination light detector can be located in the light path of at least one other direction, and can comprise at least one of a CCD, a CID, a CMOS, and a photodiode array.

In another aspect, the present apparatus and methods provides a stand alone light source comprising a CCIS as discussed herein having a variable selected spectral output and wavelength dependent intensity distribution and sized to project light onto a sample material. The CCIS can comprise the various elements discussed herein and a projection system optically connected to and downstream from the SLM, wherein the projection system projects the desired segment as a directed light beam to illuminate the material.

Similar projection systems can also be incorporated within light sources contained within a single housing containing the other components of the spectral measurement systems herein. For example, the high output light source, the spectrum former, the enhancing optical element that provides an enhanced image, the SLM, the projection system, etc., can all be located in a single housing, or fewer or more elements can be located in a single housing.

The source of illumination can also comprise a heat management system operably connected to the tunable light source to remove undesired energy emitted from the light source toward at least one of the SLM and the spectrum former. The CCIS can for example comprise a heat removal element operably connected to the light source to remove undesired energy emitted from the light source toward at least one of the SLM, the enhancing optical element, and the spectrum former. The heat removal element can for example be located between the spectrum former and a first SLM, between the lamp and the spectrum former, or elsewhere as desired. The heat removal element can comprise a dichroic mirror. The dichroic mirror can transmit desired wavelengths and reflect undesired wavelengths, or vice-versa. The undesired energy can be directed to an energy absorbing surface and thermally conducted to a radiator. The heat removal element can be an optical cell containing a liquid that absorbs undesired wavelengths and transmits desired wavelengths. The liquid can be substantially water and can flow through the optical cell via an inlet port and outlet port in a recirculating path between the optical cell and a reservoir. The recirculating path and the reservoir can comprise a cooling device, which can be a refrigeration unit, a thermoelectric cooler, or a heat exchanger.

The CCIS further can comprise a spectral recombiner optically connected to and located downstream from the spatial light modulator, which recombiner can for example comprise a prism, a Lambertian optical diffusing element, a directional light diffuser such as a holographic optical diffusing element, a lenslet array, or a rectangular light pipe. In one embodiment, the spectral recombiner can comprise an operable combination of a light pipe and at least one of a lenslet array and a holographic optical diffusing element.

The CCIS or spectral measurement system can if desired comprise an adapter or other apparatus for mechanically and/or optically connecting the illumination light guide of a spectrometer or other spectral measurement system to the output of the light source. The illumination light guide of the spectrometer can be at least one of an optical fiber, optical fiber bundle, liquid light guide, hollow reflective light guide, or free-space optical connector. The light guide may be integral with the spectrometer or it may be modular and separable from the spectrometer.

In some aspects of the apparatus and methods, the illumination light is directed to illuminate a material such that light emanating from the material, which light may or may not be the emanation light used for spectral measurements, is also used for imaging. Such images can be effected using a sensor such as a photodetector, photodiode array, CCD detector, CMOS detector, avalanche photodiode, or other type of imaging device.

In some aspects of the apparatus and methods, the illumination light is directed to illuminate a material such that light is transmitted through the material or through a container, sampling window, cuvette or other optical path containing the material such that transmitted light that is not absorbed by the material can be measured by an optical measurement sensor.

In some aspects of the apparatus and methods, the illumination light is directed to illuminate a material such that it excites fluorescence (or other emitted light) in the material and fluorescent light is emitted from the material or through a container, sampling window, cuvette or other optical path containing the material and can be measured by an optical measurement sensor.

In some embodiments of the apparatus and methods the SMS of the spectrometer can be an unfiltered sensor. An unfiltered image sensor relies on the natural optical response of the sensor material to light impinging on the sensor to generate spectroscopy data signal. The SMS can for example be a photodetector, photodiode array, CCD detector, CMOS detector, avalanche photodiode, or other type of spectral measurement device such as single sensor element, linear array of sensor elements, or two dimensional array of sensing elements such as a staring array detector.

In certain embodiments of the apparatus and methods the SMS can have an optical filter placed in front of it to limit the wavelengths of light that reach the sensor. Exemplary sensors include linearly variable filters, matrix filters, long-pass filters, short-pass filters, band-pass filters, or band-blocking filters. The matrix optical filter can be at least two of a long-pass filter, a short-pass filter, a band-pass filter, or a band-blocking filter. A long-pass filter can be useful to block undesired wavelengths such as ultraviolet light or fluorescence excitation light from impinging on the sensor. A short-pass filter can be useful to block undesired wavelengths such as infrared light from impinging on the sensor. A band-pass filter can be useful to allow only selected wavelengths such as visible light to impinge on the detector. A band-blocking filter can be useful to block fluorescence excitation light from impinging on the sensor. A linearly variable filter can be useful to block higher orders of diffraction impinging on a sensor when a diffraction grating is used as a wavelength dispersive element in the SMS.

The SMS may also be a sensor that has a wavelength dispersive element, interposed between it and the light emanated from the material being measured, that causes the light to be dispersed across an array of sensing elements, each sensing element being calibrated so it is associated with a particular wavelength of light.

In some embodiments of the apparatus and methods, the SMS can be synchronized to the CCIS to provide sequences of measurements of the wavelength dependent energy distribution of material illuminated by desired wavelengths of light and captured as digital data. This digital data can then be combined or processed as desired to provide useful information as desired.

In some embodiments of the apparatus and methods, the SMS can be synchronized to the CCIS to provide sequences of measurements of a material illuminated by desired wavelengths of light and captured as digital spectral measurement data. The digital spectral measurement data can then be combined or processed as desired to provide useful information, to determine the illumination patters of the CCIS, or otherwise as desired.

The apparatus and methods can also comprise a SMS synchronized to the CCIS where the SMS is operated as a null detector, and the spectral output of the CCIS is adjusted until the intensity value at the illumination light detector and/or the SMS is null or constant at all wavelengths, and the information about the attenuated illumination is used to derive the spectral profile of the material being illuminated.

In a preferred embodiment of the apparatus and methods, the spectral measurement system or SMS provides a data capture device or sub-system able to accept a digital or analog spectrometer signal provided by an existing commercial spectrometer or spectral measurement system or a custom designed spectroscopy system constructed in a similar manner to an existing commercial spectroscopy system. The data capture device may be integral to the CCIS or it may be a modular component of a spectroscopy system. It may be operably connected to a controller containing computer implemented programming that controls at least one of the various components of the spectral measurement system.

In other embodiments, the controller contains computer implemented programming that can analyze the spectrum/spectra data of the material captured from the SMS and if desired adjust the intensity of the illumination of the material to provide a measured spectrum that is enhanced for the operating range of the SMS.

In further embodiments, the controller contains computer implemented programming that can analyze the spectrum/spectra data of the material captured from the SMS and if desired adjust the intensity of the illumination of the material to provide a measured spectrum that is enhanced for the operating range of the sensor, and then apply the information used to adjust the illumination light to scale the captured spectroscopy data in a way suitable to present the measured spectral data while restoring the appropriate relationships between the intensities of the measurement for each desired wavelength (typically, all wavelengths) while expanding the dynamic range of the measurement.

The CCIS and SMS may be operably connected to a controller, which controller contains computer-implemented programming that controls the timing of data acquisition in the SMS and the wavelength distribution and duration of illumination in the CCIS. The controller or the spectroscopy data measurement sub-system can be located in any desired location to the rest of the system. For example, the controller can be either within a housing of the source of illumination or it can be located remotely, connected by a wire, fiber optic cable, cellular link or radio link to the rest of the system. If desired, the controller, which is typically a single computer but can be a plurality of linked computers, a plurality of unlinked computers, computer chips separate from a full computer or other suitable controller devices, can also contain one or more computer-implemented programs that provide control of spectroscopy data acquisition and/or control of specific lighting characteristics, i.e., specific desired, selected spectral outputs and wavelength dependent intensities, corresponding to known wavelength bands that are suitable for spectroscopy.

The spectral measurement system can further comprise computer controlled spectral data acquisition and processing systems that can analyze the information from the spectral measurement data or sequence of spectral measurement data and present it in a way that is meaningful to a human operator.

In a further aspect, the present apparatus and methods provides methods of taking spectral measurements of a material comprising: a) directing a light beam along a light path and via a spectrum former to provide a spectrum from the light beam; b) propagating the spectrum by a tunable light filter such as an SLM that provides a desired segment of light in the spectrum to provide an illumination light consisting essentially of a selected spectral output and a selected wavelength dependent intensity distribution, transmitting the illumination light to a sample, then sensing a spectrum representing the sample, for example a spectrum reflecting from, transmitted through, or emitted from the sample, or a spectrum derived from a compensation scheme wherein the spectrum of the sample is created to provide a null response and the illumination light adjustments to create the null response are determined.

The methods further can comprise emitting the light beam from a light source located in a same housing as and upstream from the spectrum former. The methods further can comprise switching the modified light beam between a first reflected light path and a second reflected light path. The methods further can comprise passing the light beam by an enhancing optical element between the spectrum former and the SLM or other SLM to provide a substantially enhanced image of the spectrum from the spectrum former to the SLM.

The methods can further comprise sending the illumination light to an illumination light detector optically connected to and downstream from the SLM. The illumination light detector may be located in a second reflected light path or otherwise as desired. The illumination light detector can be operably connected to a controller, the controller containing computer-implemented programming able to determine from the illumination light detector whether the illumination light contains the desired selected spectral output and the desired wavelength dependent intensity distribution, and therefrom determining whether the illumination light contains the desired selected spectral output and the desired wavelength dependent intensity distribution. The methods can comprise adjusting the SLM to improve the correspondence between the illumination light and the desired selected spectral output and the desired wavelength dependent intensity distribution. In still other aspects, the present apparatus and methods comprise emitting modified light consisting essentially of a desired selected spectral output and a desired wavelength dependent intensity distribution from a stand alone light source.

The methods can further comprise directing the output beam to illuminate a material by at least one of directly illuminating the material via a projected beam, or directing the beam into the light guide of a spectrometer, or other optical measurement system. The methods can comprise capturing spectral measurement data such as spectroscopy data of the light emitted by a material illuminated by the illumination light from the CCIS and storing the spectroscopy data for processing, analysis or display in a computer memory.

The methods can further comprise illuminating a reference material with illumination light from the CCIS, and measuring the light returning from it with an SMS and adjusting the light illuminating the reference material until a specific desired reference spectrum is obtained, such as a flat line at the high end of a measurement scale for a reference white material, and storing the information about how the illumination was created to create a reference illumination data set. This can be reiterated to create a library of multiple reference illumination data sets, and/or modified to be specific to a desired material to create a desired material illumination data set.

The methods can further comprise comparing or otherwise analyzing or processing the desired material and the reference illumination data sets to derive information about the nature and amount of materials in the desired material illumination data set.

The methods can further comprise illuminating a material with a sequence of illumination patterns that can enhance the detection of the characteristics of a desired material of interest, for example, the characteristics of a range of explosive materials if the spectroscopy device is an explosive detection device, or a range of impurities in a chemical process analyzer. Such sequence can be implemented in a rapid fashion (i.e., many samplings per second). In some embodiments, the illumination patterns are characteristic of a material of interest but vary in intensity of response proportional to the concentration of the material of interest such that the concentration or amount of the material of interest present can be determined. The illumination patterns can also be characteristic of a mixture two or more materials of interest but vary in intensity of response proportional to the concentration of various mixtures of the material of interest such that the concentration or amount of the materials of interest present can be determined. The methods can further comprise combining sequences of digital or analog spectroscopy data and processing or combining them to form spectroscopy data of the material that provides useful information.

These and other aspects, features and embodiments are set forth within this application, including the following Detailed Description and attached drawings. The discussion herein provides a variety of aspects, features, and embodiments; such multiple aspects, features and embodiments can be combined and permuted in any desired manner. In addition, various references are set forth herein that discuss certain apparatus, systems, methods, or other information; all such references are incorporated herein by reference in their entirety and for all their teachings and disclosures, regardless of where the references may appear in this application. Such incorporated references include: U.S. Pat. No. 6,781,691; pending U.S. patent application Ser. No. 10/893,132, entitled Apparatus And Methods Relating To Concentration And Shaping Of Illumination, filed Jul. 16, 2004; pending U.S. patent application Ser. No. 10/951,439, entitled Apparatus And Methods Relating To Color Imaging Endoscope Systems, filed contemporaneously herewith; pending U.S. patent application Ser. No. 10/951,438, now U.S. Pat. No. 7,108,402, entitled Apparatus And Methods Relating To Precision Control Of Illumination Exposure, filed contemporaneously herewith; pending U.S. patent application Ser. No. 10/951,448, entitled Apparatus And Methods Relating To Expanded Dynamic Range Imaging Endoscope Systems, filed contemporaneously herewith; pending U.S. patent application Ser. No. 10/951,449, entitled Apparatus And Methods For Performing Phototherapy, Photodynamic Therapy And Diagnosis, filed contemporaneously herewith.

BRIEF DESCRIPTION OF THE DRAWINGS

FIG. 5A illustrates a case where successive measurements are made with successively reduced intensity of the illumination light at selected wavelengths. FIG. 5B illustrates a case where successive measurements are made with different spectral shapes.

FIGS. 6A, 6B and 6C provide a schematic representation of dynamic range expansion by a spectral measurement system herein that generates and uses illumination light having a narrow spectral output that is swept over a broad range of wavelengths over time. FIG. 6A provides a schematic representation of the spectral measurement sensor 16 of the spectral measurement system being overexposed by certain wavelengths in the broad range of wavelengths swept over time. FIG. 6B provides a schematic representation of reducing the wavelength dependent intensity distribution of all the wavelengths in the broad range of wavelengths swept over time, which results in effectively lowering the intensity of certain wavelengths of the light emanating from the target material. FIG. 6C provides a schematic representation of reducing the wavelength dependent intensity distribution of certain wavelengths in the broad range of wavelengths swept over time, which results in easily measurable intensities for all wavelengths of the light emanating from the target material.

FIGS. 7A, 7B and 7C provide a schematic representation of dynamic range expansion by a spectral measurement system herein that generates and uses illumination light having a broad spectral output. FIG. 7A provides a schematic representation of the detection light sensor reaching saturation for certain wavelengths in the spectral output of the illumination light. FIG. 7B provides a schematic representation of reducing the wavelength dependent intensity distribution of all the wavelengths in the broad spectral output, which results in excessively lowering the intensity of certain wavelengths of the light from the target material. FIG. 7C provides a schematic representation of reducing the wavelength dependent intensity distribution of certain wavelengths in the broad spectral output, which results in good intensities for all wavelengths of the light from the target material.

FIG. 8A illustrates illuminating the reference sample with illumination light comprising a broad spectrum of wavelengths and shows the resultant detected spectrum. FIG. 8B illustrates illuminating the reference sample with illumination light adjusted by reducing the intensity of certain wavelength such that the resultant detected spectrum is flat. FIG. 8C illustrates the case where the adjusted light from FIG. 8B is used to illuminate a target sample, resulting in a detected spectrum that is no longer flat and from which the target sample's spectrum can be determined. FIG. 8D illustrates the case where the illumination of the target same sample is adjusted so as to result in a flat detected spectrum. The spectrum of the target sample can then be deduced from the adjusted illumination spectrum.

DETAILED DESCRIPTION

Figure 1A:
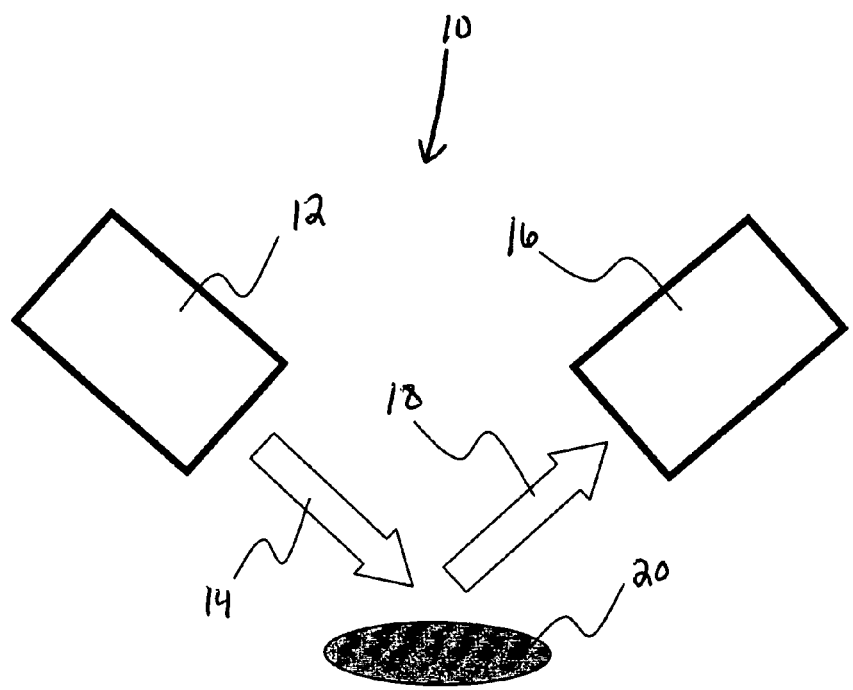
FIG. 1A provides a schematic representation of a spectral measurement system, according to an embodiment of the invention, with a CCIS that illuminates a target material and a spectral measurement sensor that detects light reflected by the target material.

The present apparatus and methods, etc., comprise spectral measurement systems such as spectroscopy systems, spectroradiometry systems, or spectrophotometry systems to measure the spectral properties of a material such as gas, liquid, solid, chemical compound, biological material such as biological fluids or tissue, paint or coating or other material. The spectral measurement systems comprise a computer-controlled illumination system (CCIS) that can generate and emit illumination light having a variable selected spectral output and a variable selected wavelength dependent intensity distribution and directed toward the target material. The spectral measurement system also comprises an spectral measurement sensor (SMS) operably linked to the CCIS and configured to detect light from the target material and generate spectral data representing at least the spectral distribution and wavelength dependent intensity distribution of the light from the target material. Furthermore, the spectral output and wavelength dependent intensity distribution of the light generated by the CCIS may be varied to correspond with different spectroscopic measurement techniques.

For example, the spectral distribution and wavelength dependent intensity distribution of the illumination light may be varied so that the target material neither emits light, reflects light nor transmits light when the target material receives the illumination light. Or, the spectral output and wavelength dependent intensity distribution of the illumination light may be varied so that the target material emits, reflects and/or transmits light having a spectral output with a substantially constant wavelength dependent intensity distribution such that the intensity of emanation is substantially equal or flat across all desired wavelengths. For another example, the spectral distribution and wavelength dependent intensity distribution of the illumination light may be varied to enhance the dynamic range for the spectral measurement system. For yet another example, the spectral distribution and wavelength dependent intensity distribution of the illumination light may be varied to measure the different spectral properties of two or more components of the target material. For still another example, the spectral distribution and wavelength dependent intensity distribution of the illumination light may be varied so that the target material emits, reflects and/or transmits light having a spectral output with a substantially constant wavelength dependent intensity distribution; and then the illumination light spectrum can be compared to the illumination light spectrum of a reference material that produces a same substantially constant wavelength dependent intensity distribution spectrum in light from the reference material.

Turning to some general information about light, the energy distribution of light is what determines the nature of its interaction with an object, compound or organism. A common way to determine the energy distribution of light is to measure the amount or intensity of light at various wavelengths to determine the energy distribution or spectrum of the light. To make light from a light source useful for a particular purpose it can be conditioned to remove undesirable wavelengths or intensities, or to enhance the relative amount of desirable wavelengths or intensities of light. For example, a high signal-to-noise ratio and high out-of-band rejection enhances the spectral characteristics of light.

The systems and methods herein, including kits and the like comprising the systems or for making or implementing the systems or methods, provide the ability to selectively, and variably, decide which colors, or wavelengths, of light will be projected from the system, and how strong each of the wavelengths will be. The wavelengths can be a single wavelength, a single band of wavelengths, a group of wavelengths/wavelength bands, or all the wavelengths in a light beam. If the light comprises a group of wavelengths/wavelengths bands, the group can be either continuous or discontinuous. The wavelengths can be attenuated so that the relative level of one wavelength to another can be increased or decreased (e.g., decreasing the intensity of one wavelength among a group of wavelengths effectively increases the other wavelengths relative to the decreased wavelength). This is advantageous because such fine control of spectral output and wavelength dependant intensity distribution permits a single illumination system to provide highly specialized illumination light for spectroscopy.

DEFINITIONS

The following paragraphs provide definitions of some of the terms used herein. All terms used herein, including those specifically described below in this section, are used in accordance with their ordinary meanings unless the context or definition indicates otherwise. Also unless indicated otherwise, except within the claims, the use of "or" includes "and" and vice-versa. Non-limiting terms are not to be construed as limiting unless expressly stated (for example, "including" and "comprising" mean "including without limitation" unless expressly stated otherwise).

A "controller" is a device that is capable of controlling a spatial light modulator, a detector or other elements of the apparatus and methods herein. A "controller" contains or is linked to computer-implemented programming. Typically, a controller comprises one or more computers or other devices comprising a central processing unit (CPU) and directs other devices to perform certain functions or actions, such as the on/off pattern of the pixels in the pixelated SLM, the on/off status of pixels of a pixelated light detector (such as a charge coupled device (CCD) or charge injection device (CID)), and/or compile data obtained from the detector, including using such data to make or reconstruct images or as feedback to control an upstream spatial light modulator. A computer comprises an electronic device that can store coded data and can be set or programmed to perform mathematical or logical operations at high speed. Controllers are well known and selection of a desirable controller for a particular aspect of the present apparatus and methods is within the scope of the art in view of the present disclosure.

A "spatial light modulator" (SLM) is a device that is able to selectively modulate light. The present apparatus and methods comprise one or more spatial light modulators disposed in the light path of an illumination system. A pixelated spatial light modulator comprises an array of individual pixels, which are a plurality of spots that have light passing characteristics such that they transmit, reflect or otherwise send light along a light path, or instead block the light and prevent it or interrupt it from continuing along the light path. Such pixelated arrays are well known, having also been referred to as a multiple pattern aperture array, and can be formed by an array of ferroelectric liquid crystal devices, electrophoretic displays, or by electrostatic microshutters. See, U.S. Pat. No. 5,587,832; U.S. Pat. No. 5,121,239; R. Vuelleumier, Novel Electromechanical Microshutter Display Device, Proc. Eurodisplay '84, Display Research Conference September 1984.

A reflective pixelated SLM comprises an array of highly reflective mirrors that are switchable been at least two different angles of reflection. One example of a reflective pixelated SLM is a digital micromirror device (DMD), as well as other MicroElectroMechanical Structures (MEMS). DMDs can be obtained from Texas Instruments, Inc., Dallas, Tex., U.S.A. In this embodiment, the mirrors have three states. In a parked or "0" state, the mirrors parallel the plane of the array, reflecting orthogonal light straight back from the array. In one energized state, or a "−10" state, the mirrors fix at −10° relative to the plane of the array. In a second energized state, or a "+10" state, the mirrors fix at +10° relative to the plane of the array. Other angles of displacement are possible and are available in different models of this device. When a mirror is in the "on" position light that strikes that mirror is directed into the illumination light path. When the mirror is in the "off" position light is directed away from the illumination light path. On and off can be selected to correspond to energized or non-energized states, or on and off can be selected to correspond to different energized states. If desired, the light directed away from the projection light path can also be collected and used for any desired purpose (in other words, the DMD can simultaneously or serially provide two or more useful light paths). The pattern in the DMD can be configured to produce two or more spectral and intensity distributions simultaneously or serially, and different portions of the DMD can be used to project or image along two or more different projection light paths.

A "spectrum former" can be any desired optical and/or electrical element that separates a light beam into its respective spectral components, such as a prism, a diffraction grating, either planar or curved, such as a reflective diffraction grating or a transmission diffraction grating, an optical filter comprising a linearly variable wavelength filter or other spatially variable wavelength filter, or a mosaic optical filter. A linearly variable wavelength filter is an optical filter where the wavelength that is transmitted varies across the face of the filter, such as filters made by OCLI, a JDS Uniphase company, where the wavelength of transmission varies in a continuous manner between positions of incident light from one end of the filter to the other end. This filter can be linearly variable, non-linearly variable or step-wise variable.

An "illumination light path" is the light path from a light source to a target or scene, while a "detection light path" is the light path for light emanating from a sample (e.g., light reflecting from a sample, emitting (e.g., fluorescing) from a sample, transmitted through a sample), to a detector. The light includes ultraviolet (UV) light, blue light, visible light, near-infrared (NIR) light and infrared (IR) light.

"Upstream" and "downstream" are used in their traditional sense wherein upstream indicates that a given device is closer to a light source, while downstream indicates that a given object is farther away from a light source.

The scope of the present apparatus and methods includes both means plus function and step plus function concepts. However, the terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. Similarly, the terms set forth in this application are not to be interpreted in method or process claims as indicating a "step plus function" relationship unless the word "step" is specifically recited in the claims, and are to be interpreted in the claims as indicating a "step plus function" relationship where the word "step" is specifically recited in a claim.

Other terms and phrases in this application are defined in accordance with the above definitions, and in other portions of this application.

Figure 1B:
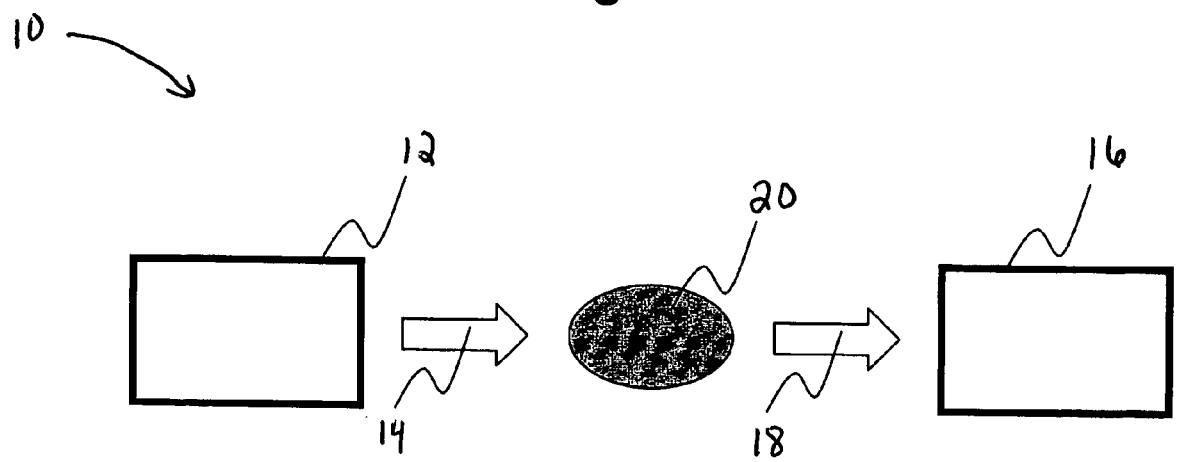
FIG. 1B provides a schematic representation of a spectral measurement system, according to an embodiment of the invention, with a CCIS that illuminates a target material with illumination light, and a detector that detects light transmitted by the target material.

FIGS. 1A and 1B provide schematic representations of a spectral measurement system 10, according to an embodiment of the invention. The spectral measurement system 10 comprises a CCIS 12 that generates and emits illumination light 14, and a spectral measurement sensor 16 configured to detect emanating light 18 from a target material 20. The illumination light 14 comprises a spectral output and wavelength dependent intensity distribution that may be varied as desired, and is directed toward the target material 20. The target material 20 receives the illumination light 14 and absorbs all or a portion the illumination light 14, reflects (FIG. 1A) all or a portion of the illumination light 14, transmits (FIG. 1B) all or a portion of the illumination light 14, and emits light (not shown), to generate the emanating light 18 from the target material, or otherwise interacts with the illumination light. The spectral measurement sensor 16 then detects the emanating light 18 and generates data representing at least the spectral distribution and wavelength dependent intensity distribution of the emanating light 18. In some embodiments, The spectral measurement system 10 comprises at least one of a data capture device and a data acquisition and processing device. The data capture device is operable to record data from at least one of the computer-controlled illumination device 12 and the spectral measurement sensor 16, for future use as desired. The data acquisition and processing device is operable to analyze data from at least one of the computer-controlled illumination device 12 and the spectral measurement sensor 16, for use as desired. The data capture device and a data acquisition and processing device can, for example, be a part of the spectral measurement computer 16 or a part of the controller 24 depicted in FIG. 2.

Figure 2:
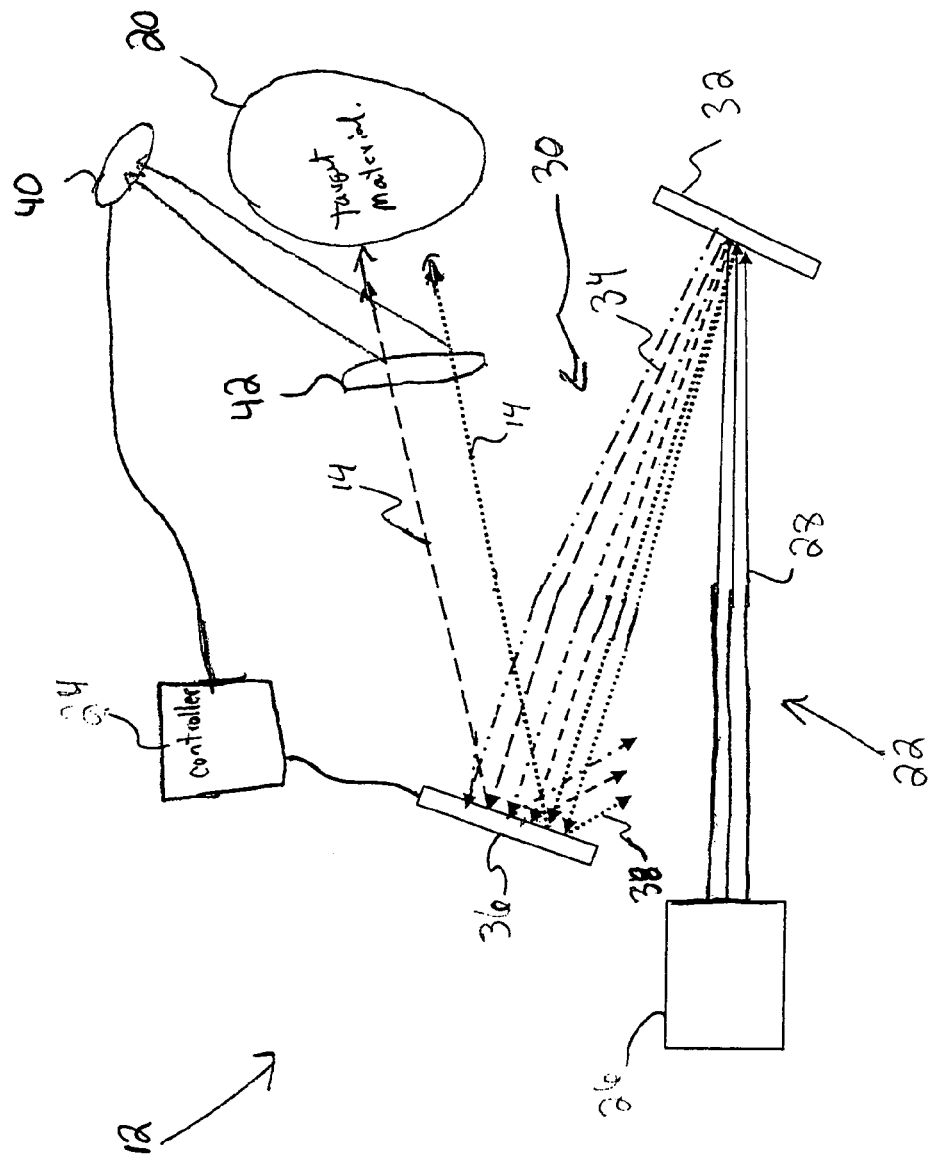
FIG. 2 provides a schematic representation of an exemplary CCIS as shown in FIGS. 1A and 1B.

FIG. 2 provides a schematic representation of a CCIS 12 according to an embodiment of the invention. The CCIS 12 comprises a tunable light source 22 for generating and emitting the illumination light 14, and a controller 24 for varying the spectral output and wavelength dependent intensity distribution of the illumination light 14 to provide a desired illumination light 14.

The tunable light source 22 provides virtually any desired color(s) and intensity(s) of light, from white light, or light that is visible to an unaided human eye, to light containing only a certain color(s) and intensity(s). The colors, or "spectral output," which means a particular wavelength, band of wavelengths, or set of wavelengths, as well as the intensities, which means a "wavelength dependent intensity distribution," can be combined and varied as desired. The tunable light source may also provide other kinds of light, such as UV light and infrared light.

The tunable light source 22 comprises a light source 26 to generate light 28, and a tunable filter 30 to generate a desired spectral output and wavelength dependent intensity distribution. The tunable filter 30 may be any desired device capable of modulating the light 28 from the light source 26. For example, the tunable filter 30 may comprise a spectrum former 32 to separate the light 28 into its spectral components 34, and a pixelated SLM 36 to combine selected spectral components to generate the illumination light 14 having the desired spectral output and wavelength dependent intensity distribution, and to separate unwanted spectral components 38 from the selected spectral components. By selectively turning on or off individual pixels of the pixelated SLM 36, one can generate illumination light 14 having a desired spectral output and a desired wavelength dependent intensity distribution. For example, only one narrow wavelength of light from the spectral components 34, such as only a pure green line of light in a typical linear spectrum may be generated, or non-linear spectra can be generated. By varying the duty cycle of some of the pixels to be turned on or off, virtually any spectral distribution of light can be created. The pixelated SLM 36 may be transmissive or reflective. In other embodiments, the tunable filter may comprise an acousto optic tunable filter, LCOS, or other desired tunable device. Suitable tunable light sources are discussed, e.g., in U.S. Pat. No. 6,781,691 and U.S. patent application Ser. No. 10/893,132.

In some embodiments, the CCIS 12 can comprise an illumination-light detector 40 for detecting the illumination light 14 and transmitting data representing the spectral output and wavelength depended intensity distribution of the illumination light 14 to the controller 24. The illumination-light detector 40 may be any desired device capable of sensing the illumination light 14 and generating data representing the spectral distribution and wavelength dependent intensity distribution of the illumination light 14. For example, the illumination-light detector 40 may comprise a spectrometer, a spectroradiometer, a charge coupled device (CCD), a charge injection device (CID), a complementary metal-oxide semiconductor (CMOS), and a photodiode array. In some embodiments, the illumination-light detector 40 receives illumination light 14 from a beam splitter such as lens 42 so that the illumination light 14 projected toward the target material is not affected by the sensor 40.

The controller 24 includes computer-implemented programming to instruct the tunable light source 22 to vary the spectral output and wavelength dependent intensity distribution of the illumination light 14. In some embodiments, the controller can be operably connected to at least one of the spectral measurement sensor 16 (FIGS. 1A and 1B) and the illumination-light detector 40, and can coordinate one or both of the sensors 16 and 40 with the tunable light source 22 to vary the spectral output and wavelength dependent intensity distribution of the illumination light 14. Such coordination with the spectral measurement sensor 16 typically comprises receiving the data generated by the spectral measurement sensor 16 and varying the spectral output and/or wavelength dependent intensity distribution to perform one or more different spectroscopic measurement techniques (discussed in greater detail in conjunction with FIGS. 3-8D). Such coordination with the sensor 40 typically comprises determining whether the spectral output and wavelength dependent intensity distribution of the illumination light 14 is the selected spectral output and wavelength dependent intensity distribution, and varying the spectral output and/or wavelength dependent intensity distribution of the illumination light 14 as desired. In some embodiments, the controller 24 is operably connected to the SLM 36, and the computer-implemented programming controls the on/off pattern of the pixels. Suitable controllers are discussed, e.g., in U.S. Pat. No. 6,781,691 and U.S. patent application Ser. No. 10/893,132.

In some embodiments, the controller 24 can comprise at least one of a data capture device and the data acquisition and processing device. With the processed data, the controller 24 can generate an image such as a digital image to be displayed for any desired reason, such as monitoring the progress of the spectroscopic measurement or evaluation by a human operator. Furthermore, the controller 24 may use the processed data to determine whether to vary the spectral output, the wavelength dependent intensity distribution or both, of the illumination light generated by the CCIS 12, and if so, then to what degree.

The CCIS 12 may comprise other components as desired. For example, the CCIS 12 may comprise at least one of a projection system to project the illumination light 14 toward the target material 20, and a heat management system to remove undesired energy generated by the tunable light source 22. The projection system may be desirable to enlarge, decrease or change the geometric form of the coverage area of the illumination light 14 on the target material 20 area and may comprise any desired optical device to accomplish this. For example, the projection system may include lenses and may focus the illumination light 14 onto an area of the target material 20 that is less than the coverage area would be without the projection system; or the projection system may disperse the illumination light onto an area of the target material 20 that is more than the coverage area would be without the projection system; and/or the projection system may modify the illumination light 14 to project the illumination light 14 in a form that corresponds to the form of a region of the target material to be illuminated, such as a long, narrow region corresponding to a rectangular sample. The heat management system may comprise any desired component or assembly of components and may be configured relative to the tunable light source 22 to remove undesired energy emitted from the light source 26. For example, the heat management system may comprise an energy-absorbing surface, preferably one thermally connected to thermally conduct the heat to a radiator, or an optical cell containing a liquid that absorbs undesired wavelengths and transmits desired wavelengths, such as water. For embodiments where the heat management system comprises an optical cell, the optical cell can also comprise an inlet port and an outlet port so that fresh liquid can be provided, and if desired the liquid can flow in a re-circulating path between the optical cell and a reservoir. The re-circulating path or the reservoir can further comprise a cooling device such as a refrigeration unit, a thermal-electric cooler and a heat exchanger. Suitable projection and heat management systems are discussed, e.g., in U.S. Pat. No. 6,781,691 and U.S. patent application Ser. No. 10/893,132.

Because the computer-controlled illumination system 12 can provide an illumination light 14 having a desired spectral output and wavelength dependent intensity distribution, and can vary the spectral output and wavelength dependent intensity distribution as desired, the spectral measurement system 10 may be easily used to perform a variety of spectroscopic measurement techniques. For example, the spectral distribution and wavelength dependent intensity distribution of the illumination light 14 may be varied so that the target material neither emits emanating light 18 (FIGS. 1A and 1B) reflects emanating light 18 nor transmits emanating light 18 when the target material 20 receives the illumination light 14. Or, the spectral output and wavelength dependent intensity distribution of the illumination light 14 may be varied so that the target material emits, reflects and/or transmits emanating light 18 having a spectral output with a substantially constant wavelength dependent intensity distribution. For another example, the spectral distribution and wavelength dependent intensity distribution of the illumination light 14 may be varied to enhance the dynamic range for the spectral measurement system 10. For yet another example, the spectral distribution and wavelength dependent intensity distribution of the illumination light 14 may be varied to measure the different spectral properties of two or more components of the target material 20. For still another example, the spectral distribution and wavelength dependent intensity distribution of the illumination light 14 may be varied so that the target material 20 emits, reflects and/or transmits emanating light 18 having a spectral output with a substantially constant wavelength dependent intensity distribution; and then the illumination light spectrum can be compared to the illumination light spectrum of a reference material that produces a same substantially constant wavelength dependent intensity distribution spectrum in light from the reference material.

Figure 3:
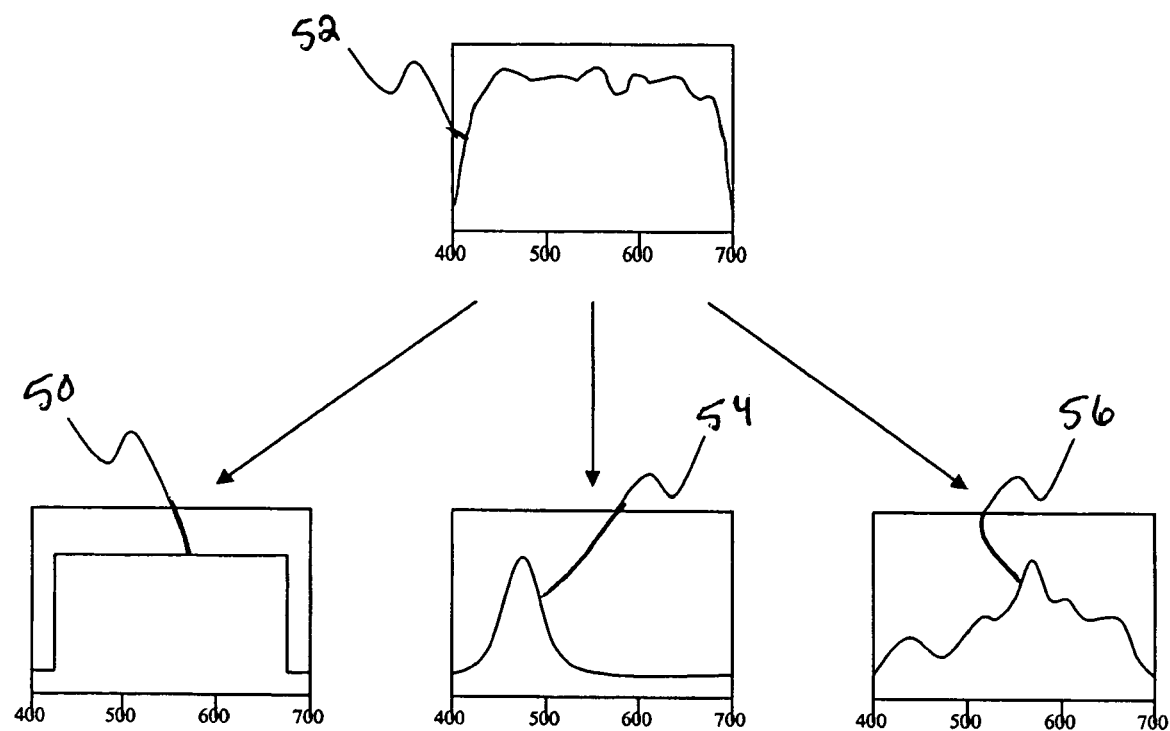
FIG. 3 provides schematic representations of light modified by a tunable light source into illumination light having a broad spectral output with a substantially constant wavelength dependent intensity distribution (a flat spectrum), a narrow spectral output (a reduced bandwidth spectrum), or an arbitrary spectral output with an arbitrary wavelength dependent intensity distribution (an arbitrary spectrum).

FIG. 3 provides a schematic representation of light 28 (FIG. 2) modified by a tunable light source 22 (FIG. 2) into illumination light 14 (FIGS. 1A-2) having any desired spectral output and wavelength dependent intensity distribution. For example, the spectral output and wavelength dependent intensity distribution of the illumination light 14 can comprise the spectrum 50. The spectrum 50 can be generated from the spectrum 52 of the light 22 from the light source 26 (FIG. 2) and can include a broad spectral output with a substantially constant wavelength dependent intensity distribution. Or, the spectral output and wavelength dependent intensity distribution of the illumination light 14 can comprise the spectrum 54, which can be generated from the spectrum 52 and can include a narrow spectral output. Or, the spectral output and wavelength dependent intensity distribution of the illumination light 14 can comprise the spectrum 56, which can be generated from the spectrum 52 and can include an arbitrary spectral output with an arbitrary wavelength dependent intensity distribution.

Because the CCIS 12 can generate illumination light 14 having an infinite variety of spectral outputs and wavelength dependent intensity distributions, the spectral measurement system 10 (FIGS. 1A and 1B) may be easily adapted for efficiently measuring the spectral properties of many different target materials.

Figure 4:
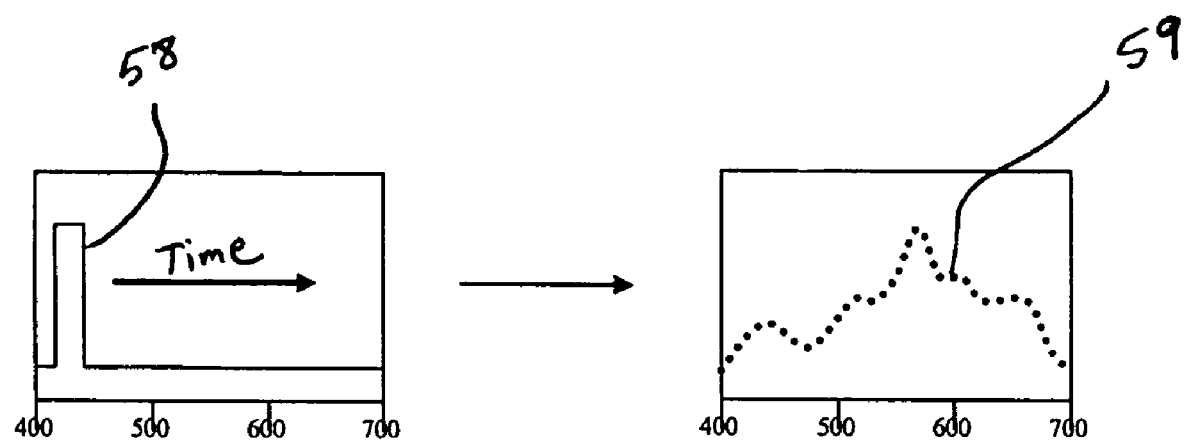
FIG. 4 provides a schematic representation of illumination light having a narrow spectral output with a substantially constant wavelength dependent intensity distribution, and whose spectral output only varies in wavelength over time (swept over a broad range of wavelengths), and the combined spectrum of the light emanating from a target material generated by such illumination light, according to an embodiment of the invention.

FIG. 4 provides a schematic representation of illumination light 14 (FIGS. 1A-2) that is generated by sequencing or sweeping a narrow spectral output with a substantially constant wavelength dependent intensity distribution over a range of wavelengths over time, according to an embodiment of the invention. For example, at a first instant, the tunable light source 22 may generate a spectrum 58 of illumination light 14 having a wavelength spectral output of approximately 425-450 nanometers. Then at a second instant, which may be any duration of time after the first instant including as few as 1 millisecond, the tunable light source 22 may generate a spectrum of illumination light 14 having a wavelength spectral output of approximately 450-475 nanometers. After the narrow spectral output with a substantially constant wavelength dependent intensity distribution has swept through the desired range of wavelengths, the individual spectra of the emanating light 18 (FIGS. 1A and 1B) from the target material 20 (FIGS. 1A and 1B) that correspond with each sequential spectrum of illumination light are combined to make the spectrum 59.

In other embodiments, the sequencing or sweeping the narrow spectral output with a substantially constant wavelength dependent intensity distribution over a range of wavelengths over time can be repeated over the same or a different range of wavelengths. Repeating the sequencing or sweeping may be desirable to measure the change of a target material's spectral properties over time and/or measure different optical characteristics of the target material's spectral property, which may be used to determine different components of the target material 20.

Figure 5A:
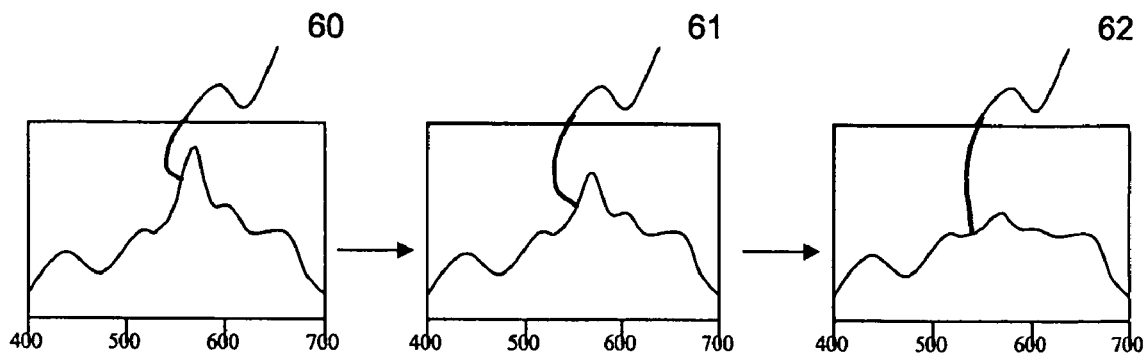
FIGS. 5A and 5B illustrate sequential spectral measurements.
Figure 5B:
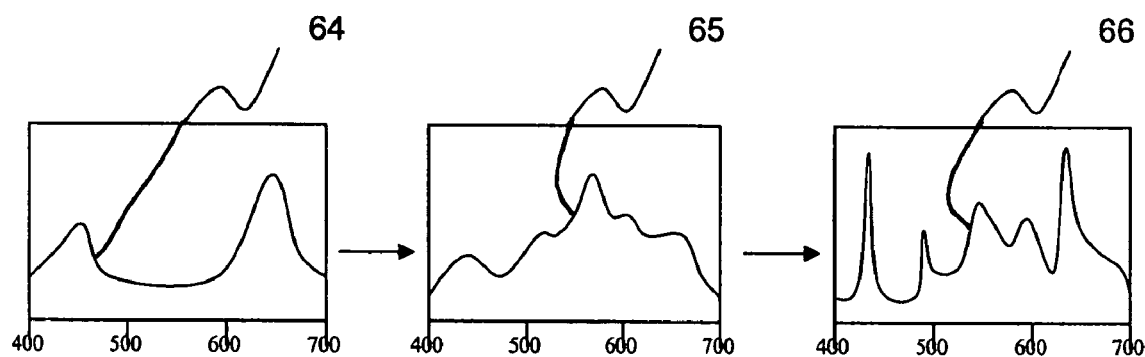

FIG. 5a provides a schematic representation of illumination light 14 (FIGS. 1A-2) having a spectral output and wavelength dependent intensity distribution, and whose spectral output only varies in wavelength dependent intensity distribution over time, according to an embodiment of the invention. Each of the spectra 60, 61, 62 represent illumination light 14 having substantially the same spectral output but different wavelength dependent intensity distributions. Varying only the wavelength dependent intensity distribution of the illumination light 14 may be desirable when the spectral properties of the target material 20 are more responsive to changes in the wavelength dependent intensity distribution of a spectral output having a broad range than to a narrow spectral output. FIG. 5b provides a schematic representation of illumination light 14 (FIGS. 1A-2) having a substantially different spectral output and a substantially different wavelength dependent intensity distribution, as shown in graphs 64, 65 and 66.

FIGS. 6A, 6B and 6C provide a schematic representation of dynamic range expansion for the spectral measurement system 10 (FIGS. 1A and 1B) according to an embodiment of the invention, that generates and uses illumination light having a narrow spectral output that is swept over a broad range of wavelengths over time.

Dynamic range expansion is a process of varying the wavelength dependent intensity distribution of a portion of the spectral output of the illumination light 14 (FIGS. 1A-2) to compensate for overexposing and/or underexposing the spectral measurement sensor 16 (FIGS. 1A and 1B). Overexposure and underexposure is somewhat like overexposing or underexposing a picture taken with a normal camera, and means that the measurement generated from the data generated by the spectral measurement sensor 16 does not accurately represent the spectral property of the target material. Previously, overexposure and underexposure have been corrected by increasing or decreasing the intensity of all the wavelengths in the illumination light directed toward a target material. But because overexposure and underexposure is often due to a single or few wavelengths in the spectrum of illumination light, increasing or decreasing the intensity of all the wavelengths in the illumination light frequently detrimentally reduces or increases the intensity of certain wavelengths in the illumination light that did not cause the overexposure and/or underexposure. Thus, the accuracy of the displayed spectral property of the target material 20 (FIGS. 1A and 1B) may be adversely affected.

With the tunable light source 22, the wavelength dependent intensity distribution of the portion of the spectral output causing the overexposure and/or underexposure can be increased or decreased as desired without increasing or decreasing the wavelength dependent intensity distribution of the remaining portions of the spectral output. Consequently, the dynamic range of the spectral measurement system 10 (FIGS. 1A and 1B) may be expanded to provide a more accurate measurement of the target material's spectral property. Expanding the dynamic range of a sensor is further discussed, e.g., in U.S. provisional patent application 60/506,273 titled Apparatus And Methods Relating To Expanded Dynamic Range Imaging Endoscope Systems and filed Sep. 26, 2003, and U.S. patent application Ser. No. 10/951,448 titled Apparatus And Methods Relating To Expanded Dynamic Range Imaging Endoscope Systems and filed Sep. 27, 2004.

FIG. 6A provides a schematic representation of the spectral measurement sensor 16 of the spectral measurement system 10 being overexposed by certain wavelengths in the broad range of wavelengths swept over time. The tunable light source 22 (FIG. 2) can generate illumination light 14, as discussed in conjunction with FIG. 4, that comprises the spectrum 68. The individual spectra of the emanating light 18 (FIGS. 1A and 1B) from the target material 20 that correspond with each sequential spectrum of illumination light 14 are combined to make the spectrum 70. The spectrum 70 includes wavelengths that would overexpose the spectral measurement sensor 16, for example the range of wavelengths comprising wavelengths about 550 nanometers to 600 nanometers.

FIG. 6B provides a schematic representation of the illumination light 14 schematically depicted in FIG. 6A after the wavelength dependent intensity distribution of all the wavelengths in the broad range of wavelengths swept over time, have been reduced. Consequently, the illumination light comprises the spectrum 72, and the individual spectra of the emanating light 18 from the target material 20 that correspond with each sequential spectrum of illumination light 14 are combined to make the spectrum 74. By reducing the wavelength dependent intensity distribution of all the wavelengths in the broad spectrum, the spectrum 74 includes wavelengths whose intensities may be so low that the sensor 16 can not accurately detect them. Thus the measurement of the target material's spectral property may be inaccurate.

FIG. 6C provides a schematic representation of the illumination light 14 schematically depicted in FIG. 6A after the wavelength dependent intensity distribution of a portion of the broad range wavelengths swept over time, has been selectively reduced. Consequently, the illumination light comprises the spectra 76, 78 and 80, and the individual spectra of the emanating light 18 from the target material 20 that correspond with each sequential spectrum of illumination light 14 are combined to make the spectrum 82. By reducing the wavelength dependent intensity distribution of only the wavelengths in the broad spectrum that cause the overexposure of the spectral measurement sensor 16, substantially all of the wavelengths in the spectrum 82 have an intensity that corresponds with the sensor's optimal range for sensitivity. Thus the measurement of the target material's spectral property may be as accurate as the sensor will permit.

FIGS. 7A, 7B and 7C provide a schematic representation of dynamic range expansion for the spectral measurement system 10 (FIGS. 1A and 1B) according to an embodiment of the invention that generates and uses illumination light 14 (FIGS. 1A-2) having a broad spectral output. The schematic representations of expanding the dynamic range of the spectral measurement system 10 that are depicted in FIGS. 7A-7C are similar to the schematic representations of expanding the dynamic range of the system 10 that are depicted in FIGS. 6A-6C. The primary difference between the dynamic range expansions depicted in FIGS. 7A-7C and 6A-6C is that the process for generating the illumination light 14 is different.

FIG. 7A provides a schematic representation of the spectral measurement sensor 16 of the spectral measurement system 10 being overexposed by certain wavelengths in the spectral output of the illumination light 14. The spectrum 84 represents the spectral output and wavelength intensity distribution of the illumination light 14, and the spectrum 86 represents the range of wavelengths and respective intensities of the emanating light 18 (FIGS. 1A and 1B) from the target material 20 after the target material 20 receives the illumination light 14 represented by the spectrum 84.

FIG. 7B provides a schematic representation of the illumination light 14 schematically depicted in FIG. 7A after the wavelength dependent intensity distribution of all the wavelengths in the spectral output have been reduced. The spectrum 88 represents the spectral output and wavelength intensity distribution of the illumination light 14, and the spectrum 90 represents the range of wavelengths and respective intensities of the emanating light 18 from the target material 20 after the target material 20 receives the illumination light 14 represented by the spectrum 88.

FIG. 7C provides a schematic representation of the illumination light 14 schematically depicted in FIG. 7A after the wavelength dependent intensity distribution of a portion of the spectral output have been reduced. The spectrum 92 represents the spectral output and wavelength intensity distribution of the illumination light 14, and the spectrum 94 represents the range of wavelengths and respective intensities of the emanating light 18 from the target material 20 after the target material 20 receives the illumination light 14 represented by the spectrum 92.

FIGS. 8A, 8B, 8C and 8D provide a schematic representation of a plurality of measurements involving a known reference target material 96 and an unknown target material 20 (FIGS. 1A-2). By knowing the reference target material 96 and the spectral output and wavelength dependent intensity distribution of the illumination light 14 (FIGS. 1A and 1B) that produces a certain spectral output and wavelength dependent intensity distribution in the emanating light 18 (FIGS. 1A and 1B) from the known reference target material 96 after it receives the illumination light 14, one can determine the unknown target material from the spectral output and wavelength dependent intensity distribution by using a same illumination light 14 that produces the same or substantially the same emanating light 18.

The known reference target material 96 may or may not be the same material as the unknown target material 20. If the known reference target material and the unknown target material are the same, then their spectral outputs and wavelength dependent intensity distributions from substantially identical illumination light will be substantially the same. If, however, the known reference target material and the unknown target material are not the same, then determining the unknown target material can comprise, for example, illuminating them with identical illumination light then comparing the resulting spectra emanating from the samples, or illuminating them with different illumination light configured to generate the same or substantially the same emanating light and then analyzing the similarities or differences of the illumination light. The same or substantially the same spectral output and wavelength dependent intensity distribution of the emanating light 18 from the known reference target material 96 and unknown target material 20 may comprise, for example, an absence of light (even though the illumination light has substantial intensity, i.e., the target materials 20 and 96 neither emit, reflect or transmit emanating light 18), a spectral output having a substantially constant wavelength dependent intensity distribution (e.g., FIGS. 8B and 8D). In other embodiments, differing illumination light differing a spectral output having a varied wavelength dependent intensity distribution are used with computer programs that compare and contrast various differences and similarities in the lights to determine one or two or more likely matches.

Figure 8A:
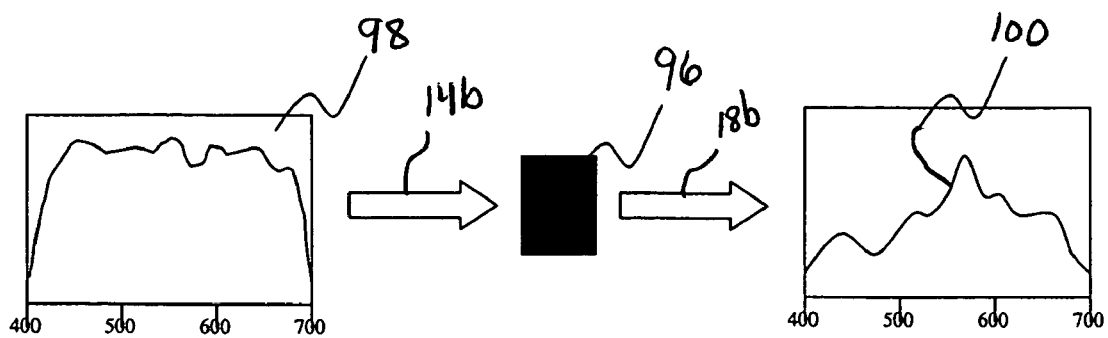
FIGS. 8A, 8B, 8C and 8D provide schematic representations of a sequence of measurements involving a target material and a reference material.
Figure 8B:
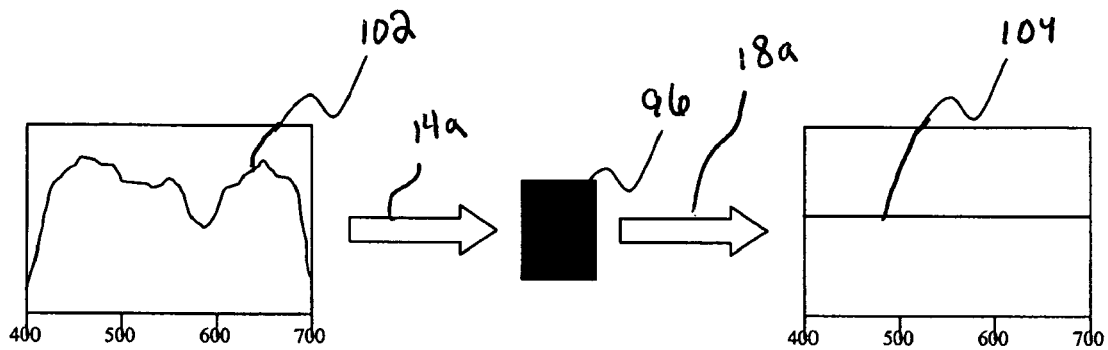

FIGS. 8A and 8B provide a schematic representation of generating a reference illumination data set, which comprises data corresponding to the material of the reference target material 96, data corresponding to the certain spectral output and wavelength dependent intensity distribution in the emanating light 18a, and data corresponding to the spectral output and wavelength dependent intensity distribution of the illumination light 14a. In some embodiments, two or more reference illumination data sets may comprise a library of data sets. Each data set in the library may be generated under substantially the same conditions, for example the reference target materials 96 and certain spectral output and wavelength dependent intensity distribution in each data set may be substantially the same. This may be desirable to provide a composite data set that provides an average of the data values for a more accurate comparison. In other embodiments, each data set in the library may be generated under different conditions, for example the reference target material 96 may change relative to each data set and/or the certain spectral output and wavelength dependent intensity distribution may change relative to each data set. This may be desirable to provide a reference material that could closely match the unknown target material.

FIG. 8A provides a schematic representation of the step of detecting the spectral distribution and wavelength dependent intensity distribution of emanating light 18b from the known reference target material 96. The tunable light source 22 (FIG. 2) generates illumination light 14b that comprises the spectrum 98. The spectral measurement sensor 16 (FIGS. 1A and 1B) detects the emanating light 18b that comprises the spectrum 100 after the known reference target material 96 receives the illumination light 14b.

FIG. 8B provides a schematic representation of the next step of varying the spectral output and wavelength dependent intensity distribution of the illumination light 14a to produce emanating light 18a from the reference material that has a substantially constant intensity throughout the light's spectrum. The tunable light source 22 varies the illumination light to generate illumination light 14a that results in spectrum 102. The spectral measurement sensor 16 detects the emanating light 18a that comprises the spectrum 104 after the known reference target material 96 receives the illumination light 14a. The spectrum 104 comprises a spectral output having a substantially constant wavelength dependent intensity distribution.

Figure 8C:
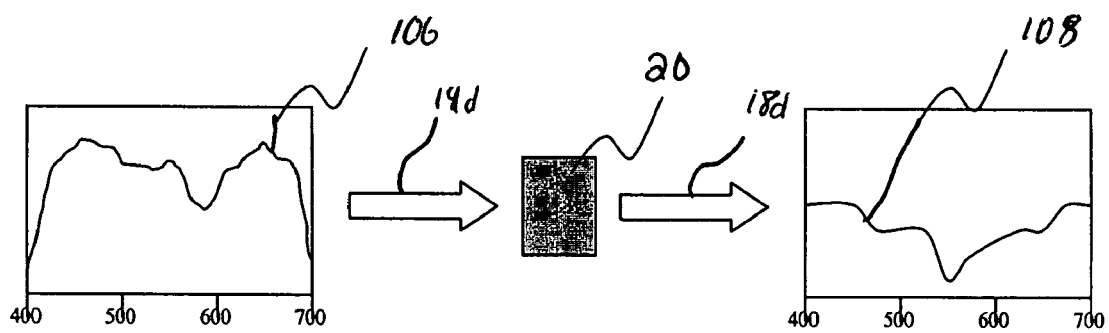
Figure 8D:
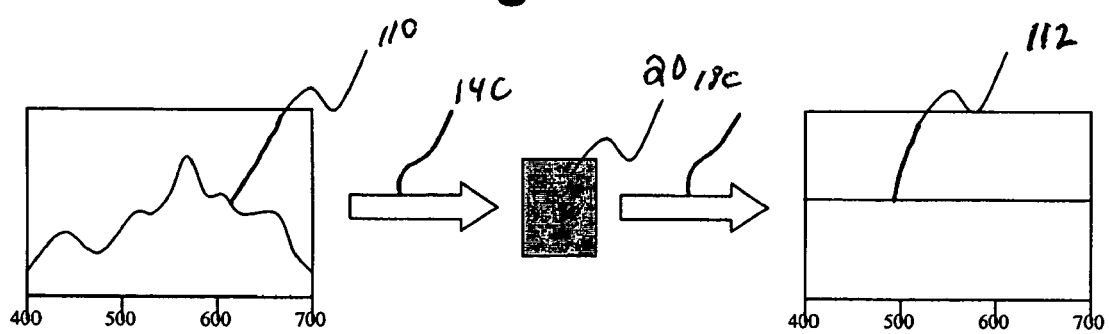

FIGS. 8C and 8D provide schematic representations of generating an illumination light 14c to produce a emanating light 18c from the unknown target material 20 having the same or substantially the same spectral distribution wavelength dependent intensity distribution as the emanating light 18a (FIG. 8B).

FIG. 8C provides a schematic representation of the step of detecting the spectral distribution and wavelength dependent intensity distribution of emanating light 18 from the unknown target material 20. The tunable light source 22 (FIG. 2) generates illumination light 14d that comprises the spectrum 106. In the embodiment shown, the illumination light 14d and the spectrum 106 are substantially identical to the illumination light 14a and the spectrum 102. If the target sample 20 were the same as reference sample 96, then the spectrum 108 would be substantially identical to spectrum 104. In the embodiment shown, however, the target sample is different from reference sample 96 so a different spectrum 108 is obtained. The spectral measurement sensor 16 (FIGS. 1A and 1B) detects the emanating light 18d that comprises the spectrum 108 after the known reference target material 96 receives the illumination light 14b.

FIG. 8D provides a schematic representation of a next step comprising using the tunable light source 22 to vary the spectral output and wavelength dependent intensity distribution of the illumination light to produce illumination light 14c having spectrum 110 that produces a substantially constant intensity emanating light 18c across the spectrum from the unknown target material 20. The spectral measurement sensor 16 detects the emanating light 18c that comprises the spectrum 112 after the unknown target material 20 receives the illumination light 14c. The spectrum 112 comprises a spectral output having a substantially constant wavelength dependent intensity distribution as the spectrum 104 (FIG. 8B).

In some aspects, the present invention includes light engines and methods related thereto as discussed herein comprising specific, tunable light sources, which can be digital or non-digital. As noted elsewhere herein, one aspect of these systems and methods relates to the ability of the engines to provide finely tuned, variable wavelength ranges that correspond to precisely desired wavelength patterns, such as, for example, noon in Sydney Australia on October $14^{th}$ under a cloudless sky, or medically useful light of precisely 442 nm. For example, such spectra are created by receiving a dispersed spectrum of light from a typically broad spectrum light source (narrower spectrum light sources can be used for certain embodiments if desired) such that desired wavelengths and wavelength intensities across the spectrum can be selected by the digital light processor to provide the desired intensity distributions of the wavelengths of light. The remaining light from the original light source(s) is then shunted off to a heat sink, light sink or otherwise disposed of (in some instances, the unused light can itself be used as an additional light source, for metering of the emanating light, etc.).

In the present invention, either or both the light shunted to the heat sink or the light delivered to the target, or other light as desired, is measured. If the light is/includes the light to the light sink, then the measurement can, if desired, include a comparison integration of the measured light with the spectral distribution from the light source to determine the light projected from the light engine. For example, the light from the light sink can be subtracted from the light from the light source to provide by implication the light sent to a target. The light source is then turned up or down, as appropriate, so that as much light as desired is provided to the target, while no more light than desired, and no more power than desired, is emanated from or used by the light source. In the past, it was often undesirable to reduce or increase the power input/output of a given light source because it would change the wavelength profile of the light source. In the present system and methods, this is not an issue because the altered wavelength output of the light source is detected and the digital light processor is modified to adapt thereto so that the light ultimately projected to the target continues to be the desired wavelength intensity distribution.

Figure 9:
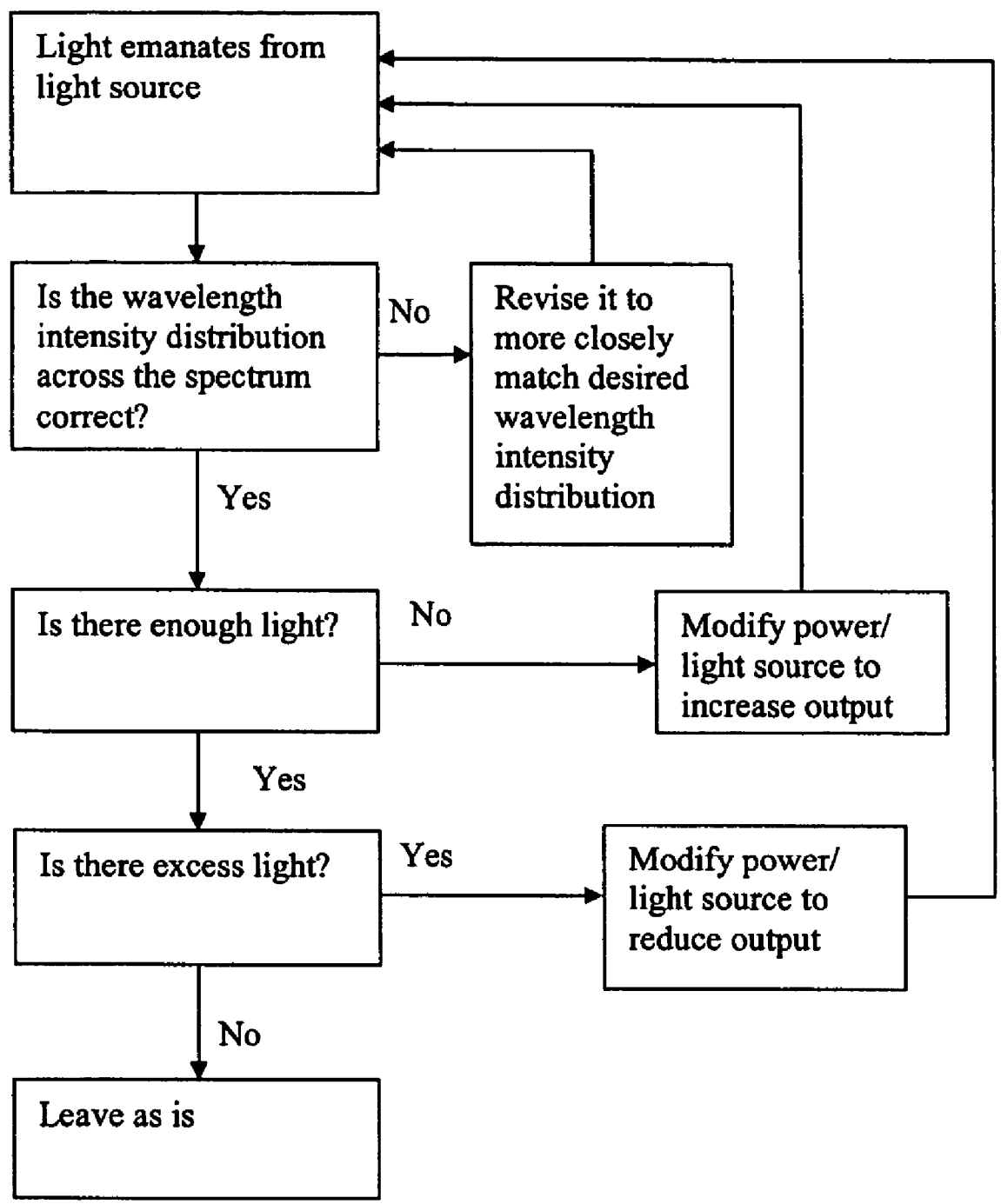
FIG. 9 is a flow chart depicting a power management scheme according to the present invention.

This aspect is depicted in a flow chart, FIG. 9, as follows: Is the wavelength intensity distribution across the spectrum correct? If yes, the proceed with the analysis; if no, then revise the wavelength intensity distribution across the spectrum as desired. Is the intensity target light distribution adequate? If no, then increase power output from light source and repeat. If yes, then proceed to next step. Is there excess light (for example being delivered to the light sink)? If yes, then decrease power to/from the light source. If no, then deem acceptable and leave as is. If power is increased or decreased: Re-check spectral distribution (e.g., of light emanated to target and/or of light from light power source) and if it is changed, reconfigure the digital light processor to adapt to the changed spectral input. If the light engine is changed, then reassess if light source can be turned up or down again. Repeat as necessary.

Some other advantages to the various embodiments herein is that the system is more power friendly, produces less heat, thereby possibly requiring fewer or less robust parts, and in addition should assist in increasing the longevity of various parts of the system due, for example, to the reduced heat generated and the reduced electricity transmitted and the reduced light transmitted. At the same time, this will provide the ability to use particular energy-favorable light sources that might not otherwise be able to be used due to fears over changed spectral distributions due to increased or decreased power output at the light source.

From the foregoing, it will be appreciated that, although specific embodiments of the apparatus and methods have been described herein for purposes of illustration, various modifications may be made without deviating from the spirit and scope of the apparatus and methods. Accordingly, the apparatus and methods include such modifications as well as all permutations and combinations of the subject matter set forth herein and are not limited except as by the appended claims.

What is claimed is:

1. A non-imaging spectral measurement system comprising at least one of a spectroscope, a spectroradiometer, or a spectrophotometer, the spectral measurement system comprising:
 a computer-controlled illumination system comprising:
  a tunable light source configured to emit illumination light comprising a variable selected spectral output and a variable selected wavelength dependent intensity distribution toward a target material, wherein the tunable light source comprises:
   a light source;
   a spectrum former comprising a prism or diffraction grating configured to provide a flail spectrum from a light beam traveling along a light path from the light source without scanning the light beam across the spectrum former,
   a pixelated spatial light modulator (SLM) located downstream from and optically connected to the spectrum former, the pixelated SLM configured to pass substantially only a selected spectral output and wavelength dependent intensity distribution of the light from the light source, the pixelated SLM operably connected to a controller which contains computer-implemented programming that controls an on/off pattern of pixels in the pixelated SLM to pass substantially only desired wavelength distribution of illumination light, and
  the controller operably connected to the tunable light source and containing computer-implemented programming configured to vary a pattern of the pixelated SLM corresponding to the variable selected spectral output and the variable selected wavelength dependent intensity distribution in the illumination light to provide a desired spectral output and wavelength dependent intensity distribution configured for measuring spectral properties of the target material; and
 a spectral measurement sensor configured to detect light emanating from the target material and determine spectral data of the light emanating from the target material to provide target spectral data, the spectral measurement sensor operably connected to the computer-controlled illumination system to communicate the target spectral data to the computer-controlled illumination system;
 wherein the controller and the computer-implemented programming are configured to receive the target spectral data and incorporate the target spectral data to tune the tunable light source to vary the variable selected spectral output and the variable selected wavelength dependent intensity distribution in the illumination light to enhance the desired spectral output and wavelength dependent intensity distribution of the illumination light, wherein the controller is configured to vary the selected spectral output and wavelength dependent intensity distribution of the illumination light in response to the target spectral data to provide an enhanced dynamic range for the spectroscope, spectroradiometer, or spectrophotometer such that the spectroscope, spectroradiometer, or spectrophotometer measures more spectral properties of the target material compared to the spectral measurement sensor alone.

2. The spectral measurement system of claim 1 wherein the spectral measurement sensor detects light reflected from the target material.

3. The spectral measurement system of claim 1 wherein the spectral measurement sensor detects light emitted from the target material.

4. The spectral measurement system of claim 1 wherein the illumination light comprises at least two forms of light comprising at least infrared light, ultraviolet light or visible light.

5. The spectral measurement system of claim 1 wherein the computer-controlled illumination system comprises an illumination light detector configured to detect the illumination light, determine illumination light spectral data, and transmit the illumination light spectral data to the controller, and wherein the controller is configured to receive the illumination light spectral data and incorporate the illumination light spectral data to tune the tunable light source to vary the variable selected spectral output and the variable selected wavelength dependent intensity distribution in the illumination light to enhance the desired spectral output and wavelength dependent intensity distribution of the illumination light.

6. The spectral measurement system of claim 1 wherein the controller at least stores the target spectral data, analyzes the target spectral data, and displays the target spectral data.

7. The spectral measurement system of claim 1 wherein the controller is configured to vary the selected spectral output and wavelength dependent intensity distribution of the illumination light in response to the target spectral data to evoke a substantially flat intensity of light emanating from the target material across all desired detected wavelengths, the substantially flat intensity of light being substantially greater than zero, and the controller determining from the varying spectral properties of the target material.

8. The spectral measurement system of claim 1 wherein the enhanced dynamic range is achieved by compensating in the illumination light for overexposure or underexposure of the spectral measurement sensor in a specific wavelength distribution but without substantially changing the illumination light in acceptable wavelength distributions.

9. The spectral measurement system of claim 1 wherein the computer-implemented programming is configured to provide a substantially constant selected spectral output and wavelength dependent intensity distribution of illumination light over time to measure changes in a spectral characteristic of spectral properties of the target material over time.

10. The spectral measurement system of claim 1 wherein the computer-implemented programming is configured to selectively vary over time the selected spectral output and wavelength dependent intensity distribution of the illumination light to measure different spectral characteristics of spectral properties of the target material.

11. The spectral measurement system of claim 1 wherein the spectral measurement system comprises a long pass filter configured to substantially block UV light and to pass at least visible light, and wherein the computer-implemented programming is configured to illuminate the target material with substantially only UV light and the measurement sensor is configured to measure at least visible light comprising fluorescent light.

12. The spectral measurement system of claim 1 wherein the controller is configured to vary the selected spectral output and wavelength dependent intensity distribution of the illumination light to illuminate the target material with a narrow wavelength band illumination light that sweeps through a desired portion of a light spectrum, wherein individual spectra of the emanating light from the target material that correspond with each sequential spectrum of illumination light are combined to make a return spectrum.

13. The spectral measurement system of claim 1 wherein the computer-implemented programming is configured to compare the target spectral data to reference spectral data of at least one known reference material.

14. The spectral measurement system of claim 13 wherein the computer-implemented programming is configured to compare the target spectral data to reference spectral data of a plurality of known reference materials, and to determine whether the target spectral data substantially matches a matching reference spectral data.

15. The spectral measurement system of claim 13 wherein the computer-implemented programming is configured to compare the target spectral data to reference spectral data of a plurality of known reference materials, and to determine whether the target spectral data substantially matches reference spectral data of a combination of at least two materials.

16. The spectral measurement system of claim 12 wherein the desired portion of the light spectrum consists essentially only of visible light.

17. The spectral measurement system of claim 12 wherein the desired portion of the light spectrum consists essentially only of UV light.

18. The spectral measurement system of claim 12 wherein the desired portion of the light spectrum consists essentially only of infrared light.

* * * * *

UNITED STATES PATENT AND TRADEMARK OFFICE
CERTIFICATE OF CORRECTION

PATENT NO. : 7,692,784 B2
APPLICATION NO. : 10/952374
DATED : April 6, 2010
INVENTOR(S) : Nicholas B. MacKinnon et al.

It is certified that error appears in the above-identified patent and that said Letters Patent is hereby corrected as shown below:

- In Claim 1, Column 22, Line 5, "configured to provide a flail spectrum" should read --configured to provide a full spectrum--.

Signed and Sealed this

Twenty-ninth Day of June, 2010

David J. Kappos
*Director of the United States Patent and Trademark Office*